US008691321B2

(12) United States Patent
Cottone

(10) Patent No.: US 8,691,321 B2
(45) Date of Patent: Apr. 8, 2014

(54) BIOABSORBABLE POLYMERIC COMPOSITION AND MEDICAL DEVICE BACKGROUND

(75) Inventor: Robert J. Cottone, Davie, FL (US)

(73) Assignee: Orbusneich Medical, Inc., Fort Lauderdale, FL (US)

( * ) Notice: Subject to any disclaimer, the term of this patent is extended or adjusted under 35 U.S.C. 154(b) by 100 days.

(21) Appl. No.: 11/875,892

(22) Filed: Oct. 20, 2007

(65) Prior Publication Data

US 2008/0206440 A1 Aug. 28, 2008

Related U.S. Application Data

(60) Provisional application No. 60/862,433, filed on Oct. 20, 2006.

(51) Int. Cl.
*A61F 2/06* (2013.01)
*B05D 3/12* (2006.01)
*B28B 1/48* (2006.01)

(52) U.S. Cl.
USPC ......... 427/2.24; 427/2.25; 427/2.1; 623/1.38; 623/1.46; 424/426; 264/150; 264/154

(58) Field of Classification Search
USPC ........ 427/2.24, 2.25; 424/426; 623/1.38, 1.46
See application file for complete search history.

(56) References Cited

U.S. PATENT DOCUMENTS

| 5,085,629 A | 2/1992 | Goldberg et al. |
| 5,317,064 A | 5/1994 | Spinu |
| 5,320,624 A | 6/1994 | Kaplan et al. |
| 5,531,998 A | 7/1996 | Mares et al. |
| 5,700,901 A | 12/1997 | Hurst et al. |
| 5,776,161 A | 7/1998 | Globerman |
| 5,964,798 A | 10/1999 | Imran |
| 6,001,395 A | 12/1999 | Coombes et al. |
| 6,033,394 A | 3/2000 | Vidlund et al. |
| 6,110,164 A | 8/2000 | Vidlund |
| 6,245,103 B1 | 6/2001 | Stinson |
| 6,251,134 B1 | 6/2001 | Alt et al. |
| 6,254,632 B1 | 7/2001 | Wu et al. |
| 6,258,382 B1 | 7/2001 | Takaoka et al. |
| 6,312,458 B1 | 11/2001 | Golds |
| 6,338,739 B1 | 1/2002 | Datta et al. |

(Continued)

FOREIGN PATENT DOCUMENTS

| CN | 1509315 A | 6/2004 |
| EP | 0600237 A1 | 6/1994 |

(Continued)

OTHER PUBLICATIONS

Tsuji. Poly(lactide) Stereocomplexes: Formation, Structure,Properties, Degradation, and Applications. Macromol. Biosci. 2005, 5, 569-597.*

(Continued)

*Primary Examiner* — Cachet Sellman
(74) *Attorney, Agent, or Firm* — Ascenda Law Group PC

(57) ABSTRACT

A method for fabricating an embodiment of a medical device comprising the steps of: preparing a biodegradable polymeric structure; coating the biodegradable polymeric structure with a polymeric coat including a pharmacological or biological agent; cutting the structure into patterns configured to allow for crimping of the cut structure and expansion of the cut structure after crimping into a deployed configuration.

7 Claims, 20 Drawing Sheets

(56) References Cited

U.S. PATENT DOCUMENTS

| | | | |
|---|---|---|---|
| 6,511,505 B2 | 1/2003 | Cox | |
| 6,537,284 B1 | 3/2003 | Inoue | |
| 6,575,688 B2 | 6/2003 | Mehdianpour | |
| 6,575,888 B2 * | 6/2003 | Zamora et al. | 600/3 |
| 6,585,755 B2 | 7/2003 | Jackson et al. | |
| 6,599,314 B2 | 7/2003 | Mathis | |
| 6,607,548 B2 * | 8/2003 | Pohjonen et al. | 606/230 |
| 6,623,521 B2 | 9/2003 | Steinke et al. | |
| 6,652,575 B2 | 11/2003 | Wang et al. | |
| 6,652,579 B1 | 11/2003 | Cox et al. | |
| 6,730,116 B1 | 5/2004 | Wolinsky | |
| 6,770,729 B2 | 8/2004 | Van Antwerp | |
| 6,805,706 B2 | 10/2004 | Solovay et al. | |
| 6,896,697 B1 | 5/2005 | Yip et al. | |
| 7,070,607 B2 | 7/2006 | Murayama et al. | |
| 2002/0007212 A1 | 1/2002 | Brown et al. | |
| 2002/0111671 A1 | 8/2002 | Stenzel | |
| 2003/0229393 A1 * | 12/2003 | Kutryk et al. | 623/1.46 |
| 2004/0098090 A1 * | 5/2004 | Williams et al. | 623/1.13 |
| 2004/0122174 A1 | 6/2004 | Mather et al. | |
| 2004/0167572 A1 * | 8/2004 | Roth et al. | 606/219 |
| 2005/0107864 A1 | 5/2005 | Hong et al. | |
| 2006/0035854 A1 | 2/2006 | Goldstein et al. | |
| 2006/0041102 A1 * | 2/2006 | Hossainy et al. | 528/354 |
| 2006/0188486 A1 | 8/2006 | Carpenter et al. | |
| 2006/0246108 A1 * | 11/2006 | Pacetti et al. | 424/426 |
| 2006/0265048 A1 * | 11/2006 | Cheng et al. | 623/1.15 |
| 2008/0051868 A1 | 2/2008 | Cottone | |
| 2008/0051873 A1 | 2/2008 | Cottone | |
| 2008/0051874 A1 | 2/2008 | Cottone | |
| 2008/0051875 A1 | 2/2008 | Cottone | |
| 2008/0097575 A1 | 4/2008 | Cottone | |
| 2008/0097576 A1 | 4/2008 | Cottone | |
| 2008/0118546 A1 | 5/2008 | Thatcher | |
| 2009/0281249 A1 | 11/2009 | Thatcher | |
| 2010/0003327 A1 | 1/2010 | Thatcher | |

FOREIGN PATENT DOCUMENTS

| | | |
|---|---|---|
| EP | 1065316 | 1/2001 |
| EP | 01737387 | 10/2005 |
| EP | 1681035 A1 | 7/2006 |

OTHER PUBLICATIONS

Yuancai Dong, Si-Shen Feng. Nanoparticles of poly(D,L-lactade)/methoxy poly(ethylene glycol)-poly(D,L-lactide) blends for controlled release of paclitaxel. Journal of Biomedical Materials Research Part A. vol. 78A, Issue 1, pp. 12-19. Apr. 2006.

PCT/US10/035169, International Search Report dated Jul. 8, 2010.

Grabow, et al. "Mechanical Properties of a Biodegradable Balloon-expandable Stent from Poly(L-lactide) for Peripheral Vascular Applications," Journal of Medical Devices. 2007, vol. 1; pp. 84-88.

Columbo, et al. "The bioabsorbable stent as a virtual prosthesis," The Lancet. 2009, vol. 373; pp. 869-870.

International Preliminary Report on Patentability for international application No. PCT/US07/74050 issued by the International Preliminary Examining Authority mailed on Jul. 21, 2009.

Written Opinion for the International Application No. PCT/US07/82034 issued by the International Preliminary Examining Authority mailed on Jan. 19, 2010.

Supplementary European Search Report dated Aug. 16, 2012.

* cited by examiner

PLLA E2 R-Stent

PLLA CoCr R-Stent

- Average body collapse pressure:
  - PLLA E2 R-stent (n=3): 4.5psi (SD 0.3psi)
  - PLLA CoCr R-stent (n=3): 2.7psi (SD 0.4psi)
- Upon removal of pressure, all crushed stents recovered 40+% of lumen diameter %Recoil = (Stent OD @ 10atm − Recoiled OD) / Stent OD @ 10atm

BIOABSORBABLE POLYMERIC COMPOSITION AND MEDICAL DEVICE BACKGROUND

BACKGROUND

All references cited in this specification, and their references, are incorporated by reference herein in their entirety where appropriate for teachings of additional or alternative details, features, and/or technical background.

The invention relates to a medical device for implantation into vessels or luminal structures within the body. In one embodiment, the present invention relates to stents and synthetic grafts which are coated with a controlled-release matrix comprising a medicinal substance for direct delivery to the surrounding tissues, which may include a ligand attached thereto for capturing progenitor endothelial cells in the blood contacting surface of the device to form mature, functional, endothelium at site of injury. In particular, the polymer matrix/drug/ligand-coated devices such as stents are for use, for example, in therapy of diseases and conditions such as restenosis, artherosclerosis, and endoluminal reconstructive therapies.

Disclosed in embodiments herein is a novel tube-shaped expandable scaffold configured to fit within the vasculature, including the cardiovasculature, having a low, propensity for biological rejection. Such scaffold may consist of, or comprise, a bioabsorbable polymer composition or blend that effectuates a combination of mechanical properties balancing elasticity, rigidity and flexibility. The polymer composition may include a base material including a bioabsorbable polymer, copolymer, or terpolymer, and a copolymer or terpolymer additive. Advantageously the polymer may be selected to undergo enzymatic degradation and absorption. In particular, the composition may allow for a "soft" breakdown mechanism allowing for the breakdown of the component polymers to be less injurious to the surrounding tissue.

A persistent problem associated with the use of metallic devices such as stents is found in the formation of scar tissue coating of the vascularly located stent, the so-called process of restenosis. Many have concluded that the continued risk of stent thrombosis due to the permanent aspect of metal stents has not been overcome by coating of the metal with drugs intended to prevent such calamities. On the contrary, an increase in death rate has also been associated with a number of these coatings. Moreover, metallic and polymeric stents may prevent vascular lumen remodeling and expansion.

With respect to stents, stents may prevent the healing of tissue and reduce complement activation of the immune response. Stents have also been associated in some instances with a reduced inflammatory response and trauma upon break-up of an implant and/or its component materials. Conventional stents may also not provide a desired degree of flexibility in shape allowing for easier implantation, particularly into blood vessels.

The present inventors have recognized a need to develop medical devices such as stents and vascular synthetic grafts, manufactured from biocompatible, biodegradable bioabsorbable polymer blends as base polymer which are useful for the treatment of disease, in particular of the vascular system. The medical devices may ameliorate problems associated with present devices.

As disclosed herein, it has been recognized by the present inventors that the base polymer may be selected to allow additional molecular free volume to encourage sufficient molecular motion so as to allow for re-crystallization to occur at physiological conditions (e.g., upon the addition of molecular strain). Increased molecular free volume may allow for an increase in the rate of water uptake adding both a plasticizing effect as well as increasing the bulk degradation kinetics.

In embodiments herewith, the compositions allow for a "soft" breakdown mechanism such that the breakdown proceeds while being friendly to the surrounding tissue (less inflammatory response, and rendering lower potential for trauma upon break up of an implant). By selecting a polymer or copolymer having an enhanced hydrophilic property for either the base or the additive or both, the polymer blend may reduce complement activation and minimize or prevent opsonization.

In certain embodiments, the bioabsorbable scaffolds allow flexibility and stretchability suitable for the implantation in the pulse movements, contractions and relaxations of, for example, the cardiovascular system.

REFERENCES

Reference is made to U.S. Pat. No. 6,607,548 B2 (Inion), issued Aug. 19, 2003, which discloses biocompatible and bioresorbable compositions comprising a lactic acid or glycolic acid based polymer or copolymer blended with one or more copolymer additives. Such implants are asserted to be cold-bendable without crazing or cracking. Reference is also made to EP 0401844, which discloses a blend of poly-L-lactide with poly D-DL-lactide, and U.S. Pat. No. 6,001,395 which discloses drug delivery with lamellar particles of a biodegradable poly(L-lactide) or copolymers or blends thereof, being at least in part crystalline. U.S. Pat. No. 7,070,607 discloses an aneurysm repair coil comprising a bioabsorbable polymeric material carrying an embolic agent wherein the thrombogenicity is controlled by the polymer composition.

SUMMARY

Embodiments disclosed herein are method of manufacturing bioabsorbable medical devices, such as stents and synthetic grafts comprising a bioabsorbable polymer composition. The medical devices are biocompatible, biodegradable and can deliver mechanical support as well as pharmaceutical substances to an injured organ after implantation into a patient.

In one embodiment, the medical devices are configured to encapsulate therapeutic agents within the walls of their structure for the treatment of diseases such as artherosclerosis, restenosis and the like. In one embodiment, as the bioabsorbable device breaks down, the device provides controlled released of the pharmaceutical trapped within its wall or integrally part of the polymeric composition. In this and other embodiments, pharmaceutical substances can be covalently attached or admixed to the polymeric material comprising the medical device. In certain embodiments, the medical device may have a coating for stimulating restoration of normal endothelium at the site of implant.

In one embodiment, there is provided a method for the manufacturing of a polymeric medical device with a coating. The method comprises the making of a polymeric medical device from a bioabsorbable polymeric composition comprising a base polymer which can be a crystallizable polymer. The method comprises making a crystallizable polymeric composition; forming a structure such as a structure which is the form of a medical device, for example, a stent; coating said structure in its luminal surface with one or more layers of a composition comprising a polymeric matrix and with or without one or more pharmacreutical substance and a ligand for recognizing and binding to target cells in the circulation. The method further comprises the step of coating the medical structure in an opposing surface, in the case of a stent, coating the abluminal surface with a composition comprising the same or different pharmaceutical substance for local delivery to the surrounding tissue.

In one embodiment, the method of manufacturing further comprises the step of designing and cutting the polymer device to a specific structure prior to coating the device or after coating the device. In this embodiment, the pharmaceutical substance and compositions comprising the coating can be applied prior to designing and cutting the device structure, or after the device is coated.

In one embodiment, there is disclosed a cardiovascular tube-shaped expandable scaffold such as a stent, fabricated from a bioabsorbable polymer composition or blend having a combination of mechanical properties balancing elasticity, rigidity and flexibility allowing bending and crimping of the scaffold tube onto an expandable delivery system (such as a balloon catheter) which is attached to a suitable vascular lumen insertion means. The deployed scaffold may be expanded from a narrowly crimped delivery conformation to a lumen diameter sufficient for implantation onto the vascular wall tissue. The flexible form of a polymer scaffold may also afford the capability of overstretching its configuration so as to facilitate insertion into blood vessel with minimal vessel wall contact. In addition, the scaffold can be manipulated to vary from a cylindrical to a truncated conical shape allowing for easy implant installation, relocation, and adjustment.

In one embodiment, the medical device is provided in an expandable scaffold, which provides a crimpable and expandable structure without stress crazing. In embodiments wherein the medical device is a stent, the expandable scaffold provides a set of interlocking struts for stabilizing the device in its deployed or expanded or implanted conformation.

Another embodiment of the scaffold polymer provides enhanced mechanical properties through a molecular reorientation and crystallization during the radial strain of expansion from a crimpable state to an expanded state.

In one embodiment, the medical device is provided as a scaffold implant in a delivery system comprising a catheter adapted with a balloon type reversible inflation or dilation means. In one embodiment, a balloon inflating device may be employed which may be heated or cooled.

In an alternate embodiment, the medical device is provided with a polymer breakdown moieties that are "friendly" at the contact vascular wall area. In certain embodiments, the breakdown kinetics are sufficiently slow to avoid tissue overload or other inflammatory reactions.

In one embodiment there is provided a minimum of 30-day retention of clinically supportive strength that may endure in place, for example, about 3-4 months. Evaluation criteria for such embodiment scaffolds may be based, for example, on mass loss in terms of decreased molecular weight, retention of mechanical properties, and tissue reaction.

In alternate embodiments, the medical device comprising a expandable scaffold is operably configured to change to from a solid state to a "rubbery state," allowing for easier surgical intervention. In this embodiment, the rubbery state of the device is attained one the device is in physiological conditions in vivo.

Optionally the polymers and construction of the device may be selected to have flexibility and elasticity suitable for an implant in friction-free contact with vascular walls during the cardiovascular pulsing contractions and relaxations.

Preferably the scaffold in an embodiment is stretchable and elastic but has a sufficiently rigid strength to be capable of withstanding the cardiovascular fluctuating pressures within a blood vessel.

According to an embodiment, the bioabsorbable polymer is composed of a poly(L-lactide) or a poly(D-lactide) base polymer. Modifying copolymers include poly L (or D)-lactide-co-Tri-methylene-carbonate or poly-L (or D)-lactide-co-e-caprolactone may be used to link the base polymers. These copolymers can be synthesized as block copolymers or as "blocky" random copolymers wherein the lactide chain length is sufficiently long enough to crystallize. The development of a crystalline morphology may enhance the mechanical properties of the medical device; enhance processing conditions, and provide the potential of cross-moiety crystallization, for example, thermal cross-links. In this embodiment, the polymer composition allows the development of the lactide racemate crystal structure, between the L and D moieties, to further enhance the mechanical properties of the medical device.

It is also envisioned that the degradation time of the polymer in the composition may be shortened by enhancing degradation kinetics. For example, the starting material may be a lower molecular weight composition and/or a base polymer may be employed that is more hydrophilic or liable to hydrolytic chain scission.

According to embodiments of the invention there is provided a compositions and methods for fabricating a base copolymer having one moiety, such as L-lactide or D-lactide, is sufficiently long enough and not sterically hindered to crystallize, with a lesser moiety, for example Glycolide or Polyethylene Glycol (PEG) or monomethoxy-terminated PEG (PEG-MME).

The compositions, in addition to the base polymer, the modifying polymer or co-polymer, may include other materials and compounds that enhance degradation kinetics such as e-caprolactone copolymer moiety, wherein the caprolactone remains amorphous with resulting segments more susceptible to hydrolysis. Such compositions may be manufactured, for example, by admixing with the base polymer blend, or reacting to the base polymer.

The composition may incorporate PEG copolymers, for example either AB diblock or ABA triblock with the PEG moiety being approximately 1%. The mechanical properties of the lactide (see Enderlie and Buchholz SFB May 2006) may be maintained. The incorporation of either PEG or PEG-MME copolymers may also be used to facilitate drug attachment to the polymer, for example in conjunction with a drug eluting medical device.

Another embodiment provides a scaffold base polymer combining polymers of low PEG content of less than 5% in high MW, i.e., 2-3 IV copolymers, which enables the lactide block to crystallize and impart equivalent strength to the base polymer.

The scaffold of embodiments herein may provide a polymer core material containing at least one encapsulated drug for localized treatment of the vascular wall and lumen. The scaffold core degradation schedule may provide, for example, a simultaneously slow release of medication for the treatment and prevention of tissue inflammation and platelet aggregation.

Another embodiment of the polymer composition or blend provides uniform degradation in situ avoiding polymer release in chunks. The scaffold may carry at least one attached or embedded identification marker made from a radioopaque material.

DETAILED DESCRIPTION

Figure 1:
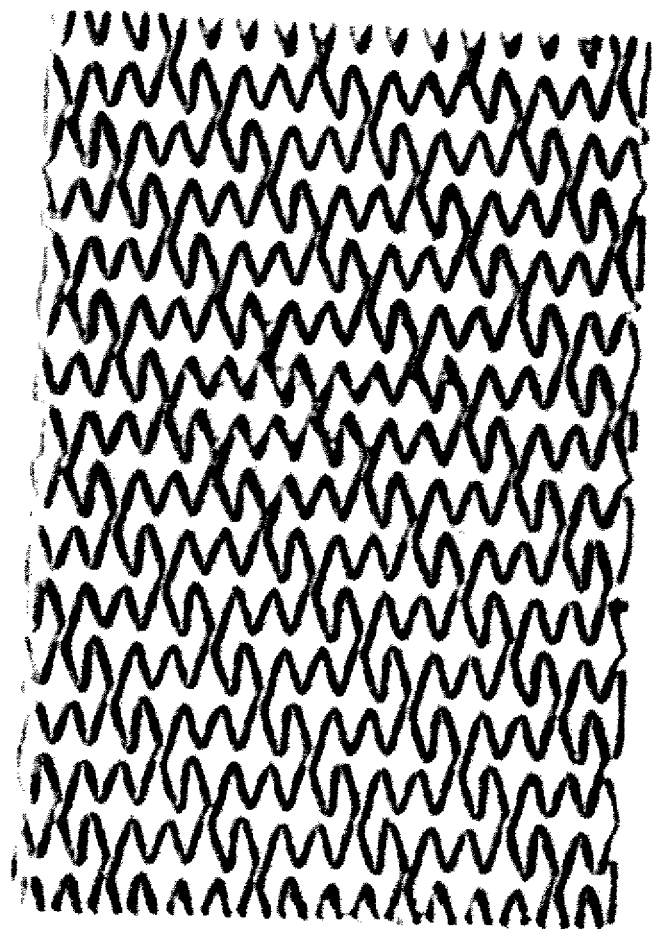
FIG. 1 illustrates a representative bioabsorbable stent design.
Figure 2:
FIG. 2 is a photograph of a representative bioabsorbable stent device.
Figure 3A:
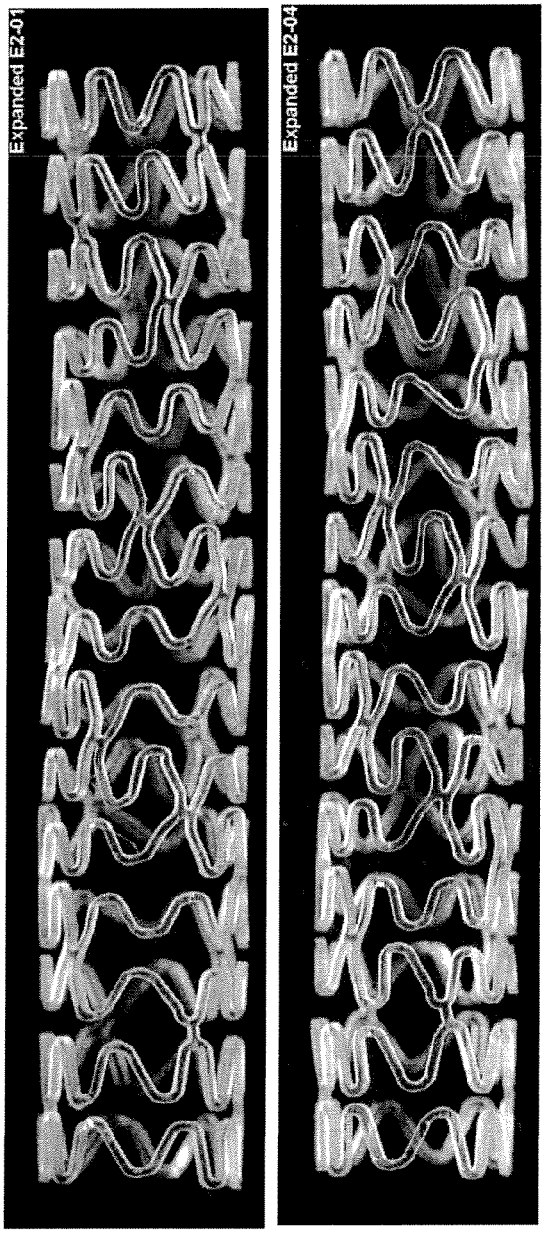
FIG. 3A and FIG. 3B are photographs of bioabsorbable stents comprising poly(L-Lactic)acid.
Figure 3B:
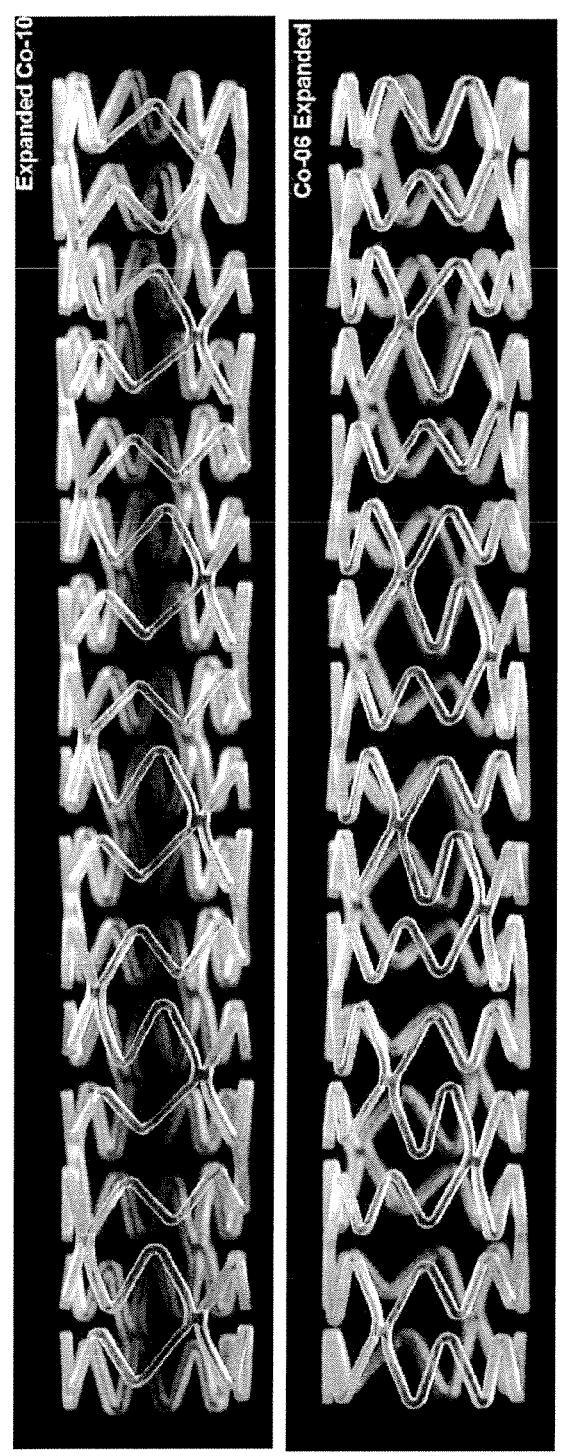
Figure 4A:
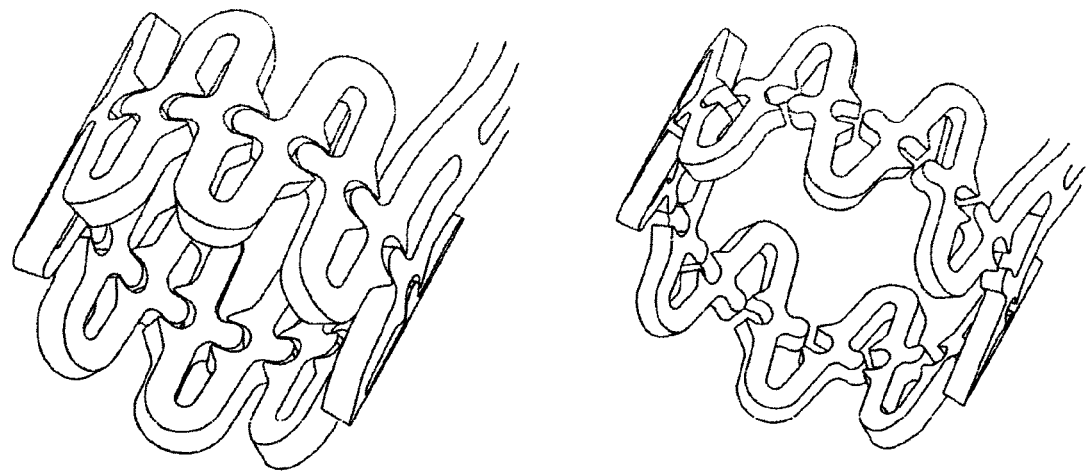
FIG. 4A illustrates a bioabsorbable stent design comprising stabilizing interlocking mechanism.
Figure 4B:
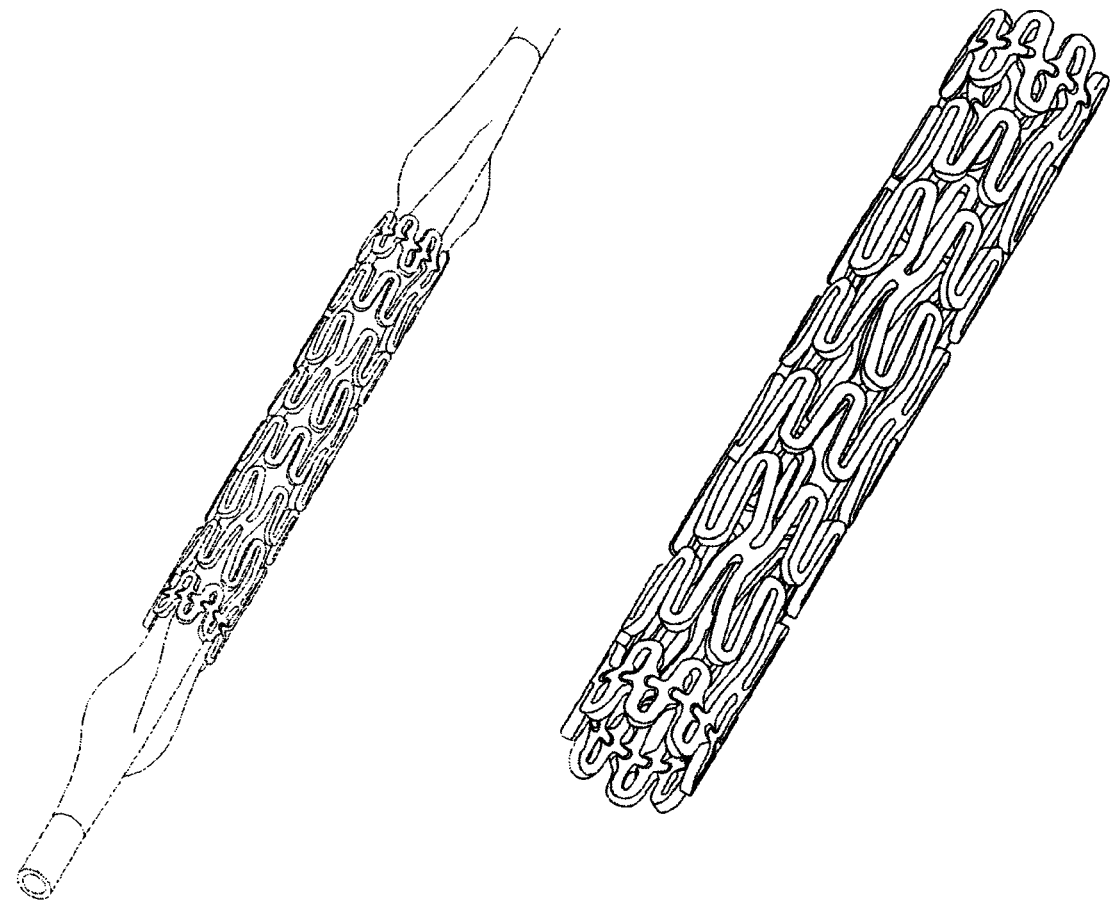
FIG. 4B illustrate a bioabsorbable stent design mounted on a balloon catheter and also showing the interlocking mechanisms at the free ends.
Figure 5A:
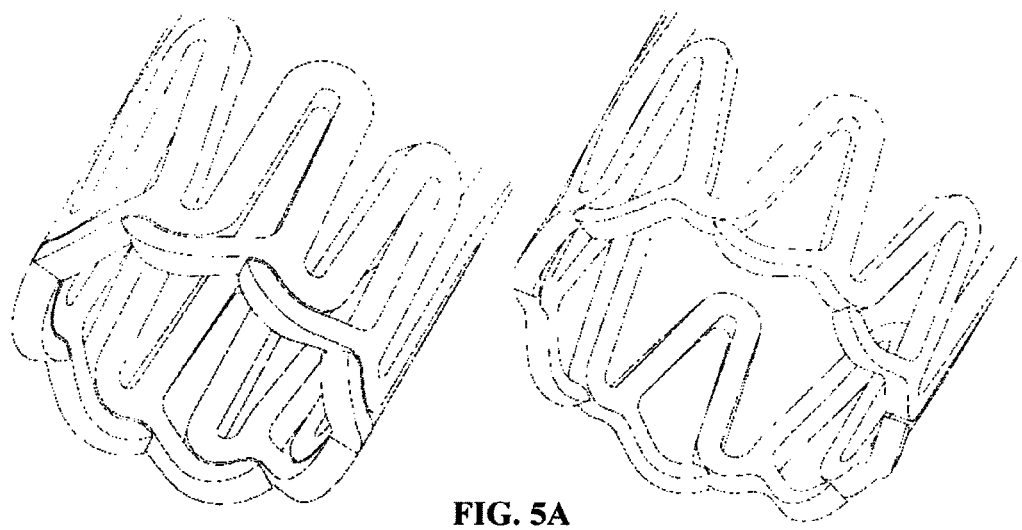
FIG. 5A and FIG. 5B illustrate a bioabsorbable stent design comprising stabilizing interlocking mechanism at the ends.
Figure 5B:
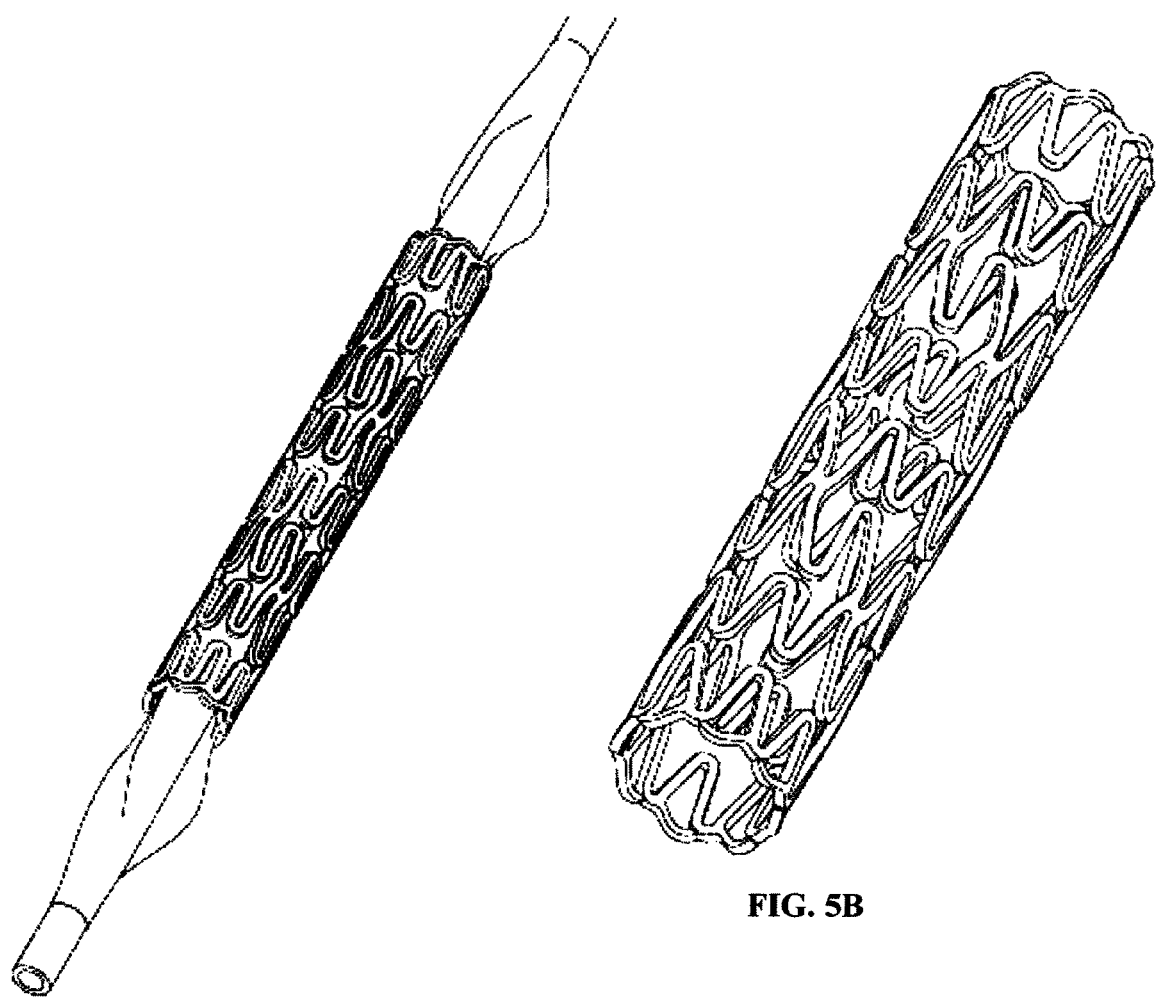
Figure 6:
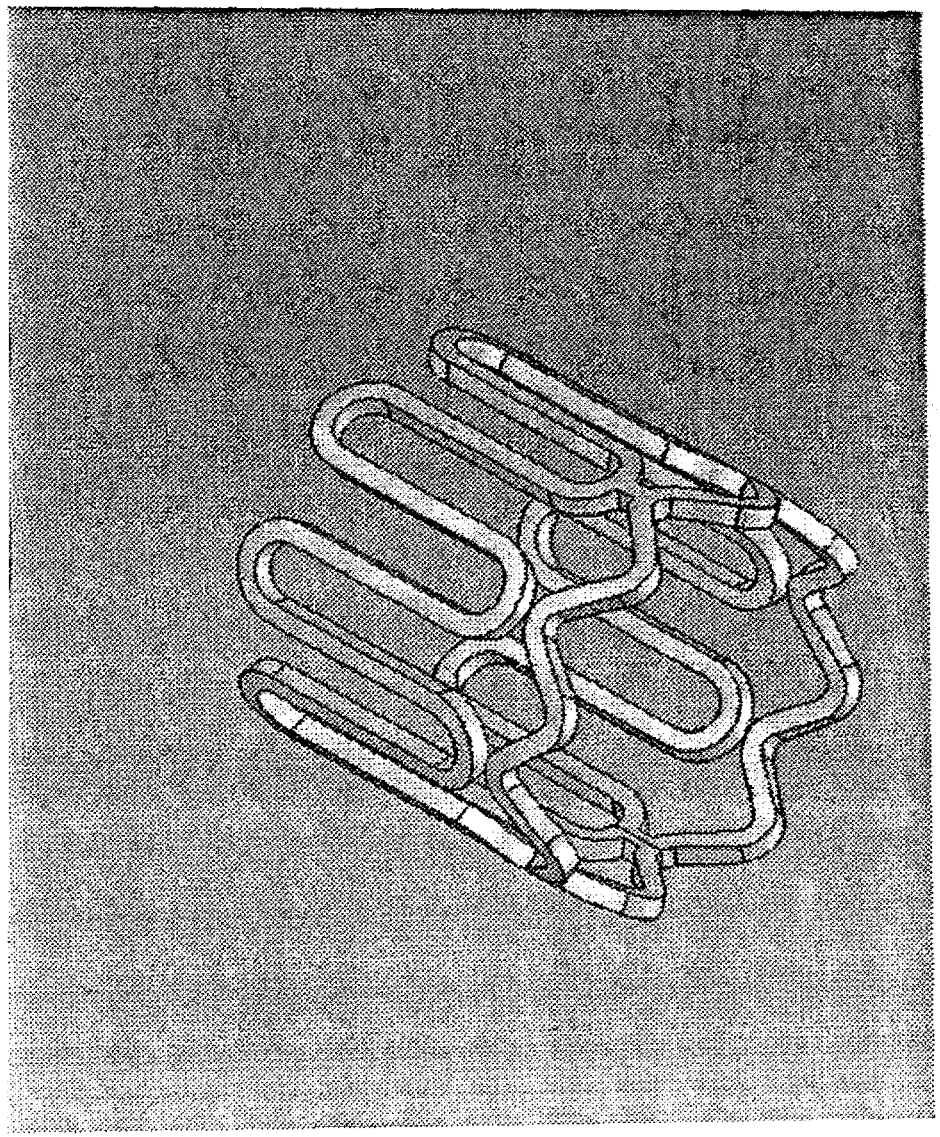
FIG. 6 illustrates a bioabsorbable stent design depicting a folded ring segment.
Figure 7:
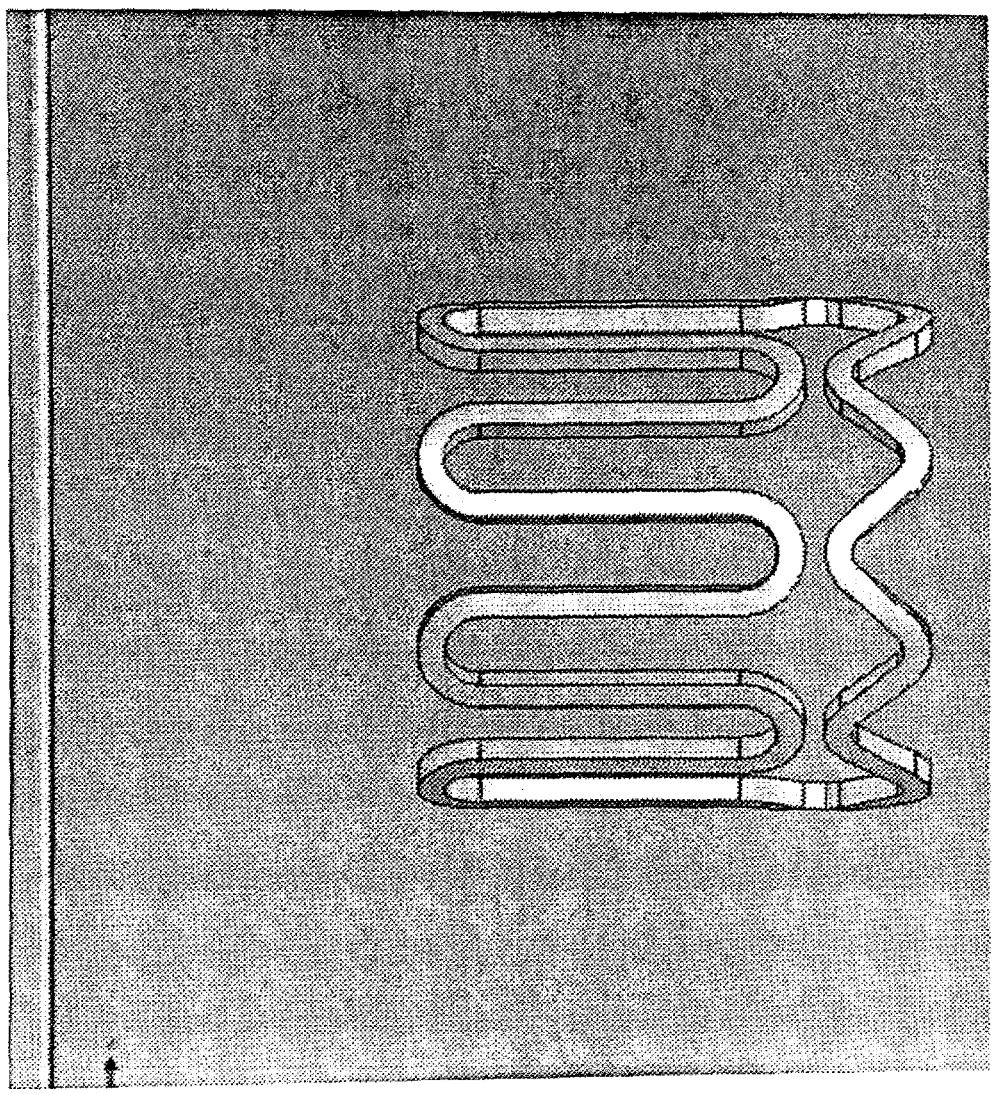
FIG. 7 illustrates a bioabsorbable stent design depicting a ring segment.
Figure 8:
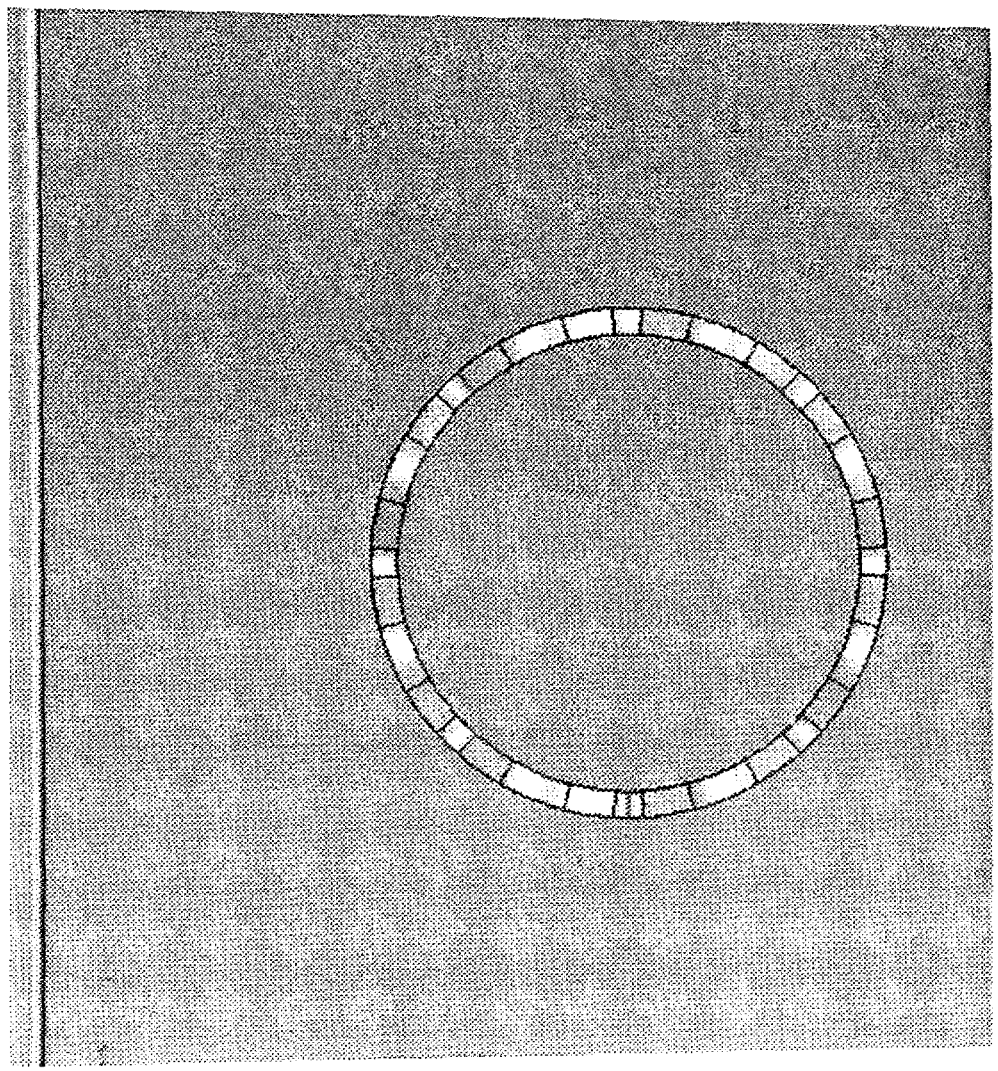
FIG. 8 illustrates a bioabsorbable stent design depicting a fully expanded diameter.
Figure 9B:
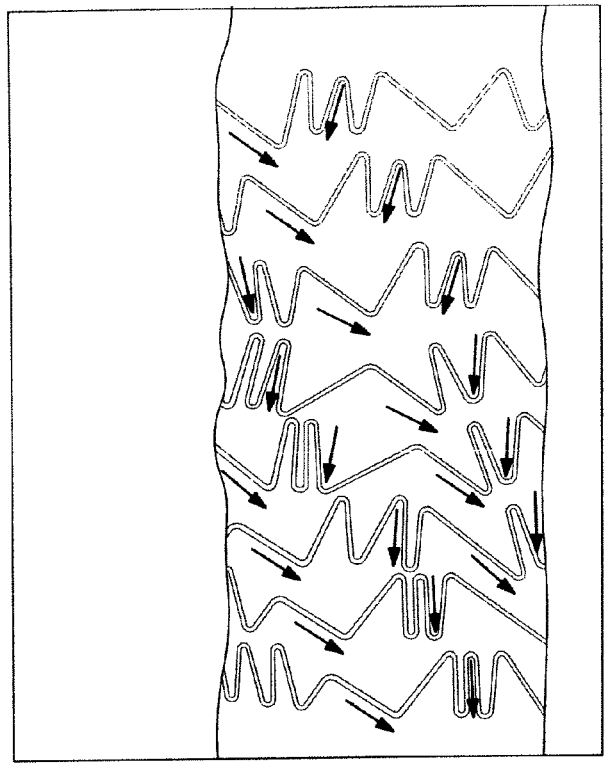
FIG. 9A and FIG. 9B illustrate a bioabsorbable stent struts design depicting a the direction of stress points on the components of the scaffold.
Figure 9A:
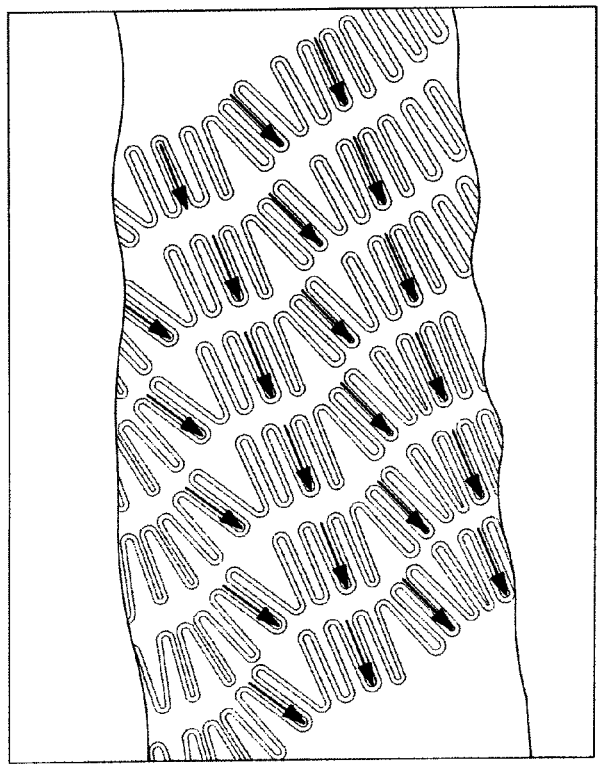
Figure 10A:
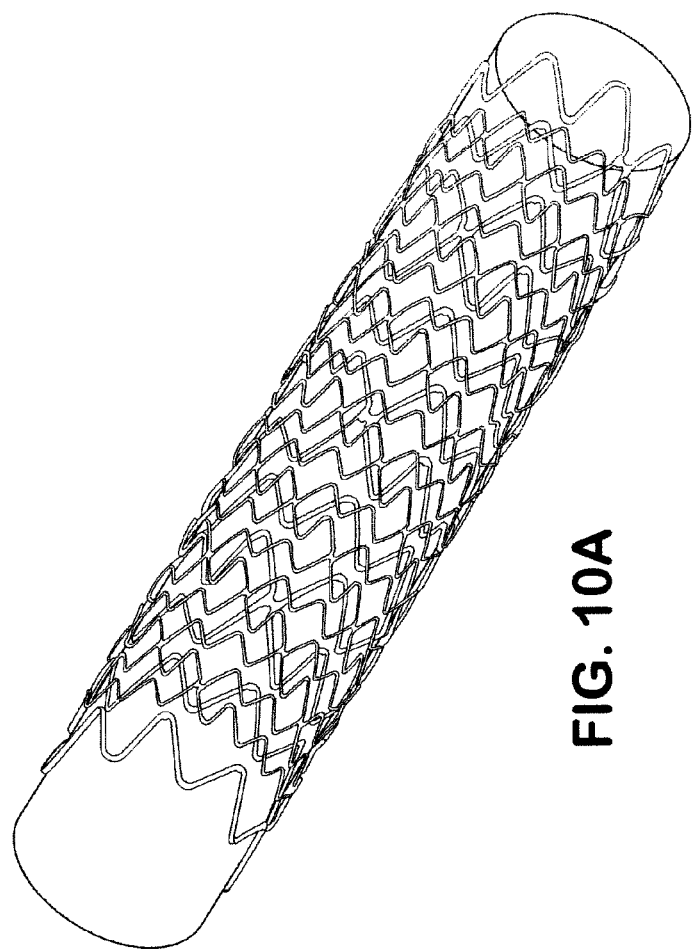
FIG. 10 illustrates a an embodiment a bioabsorbable stent design.
Figure 10B:
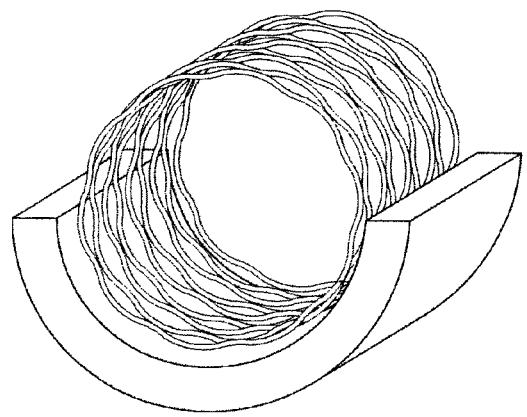

Polymer compositions of the present invention may be used to manufacture medical device for implantation into a patient. The medical devices are scaffolds having biodegradable, bioabsorbable properties and include, but are not limited to, stents, stent grafts, vascular synthetic grafts, catheters, shunts, vascular shunts, valves, grafts and the like.

The invention is also directed to methods of making the biodegradable polymer compositions and methods for making the medical devices from the polymer compositions disclosed herein.

In one embodiment, the medical device comprises a crimpable polymeric stent, which can be inserted onto a balloon delivery system for implantation. The balloon may comprise a thermal balloon or non-thermal balloon. The medical device can have a structure which is crimpable during loading and expandable without stress under physiological conditions. The medical device may comprise a structure that comprises polymers that which can orient and/or crystallize upon strain of deployment, for example during balloon dilation, in order to improve the medical devices mechanical properties. By employing a medical device comprising polymers having slow breakdown kinetics one may avoid tissue overload or other inflammatory responses at the site of implantation.

The medical devices of the invention, can be structurally configured to provide the ability to change and conform to the area of implantation and to allow for the normal reestablishment of local tissues. The medical devices can transition from solid to a "rubbery state" allowing for easier surgical intervention, than, for example a stainless steel stent. A medical device may be designed to have, for example, a minimum of 30-day retention of clinically sufficient strength.

In one embodiment, the medical device is comprised of a polymer composition can comprise a base polymer which can be present from about 60% to about 95% by weight, or from about 70% to about 80% by weight of the composition. For example, the polymer formulation can comprise from about 70% by weight poly L-lactide (about 1.5 to 3.5 or from about 2.5 to 3 IV) with the poly L-lactide-co-TMC (80/20 w/w) (1.0 to 2.6 IV or from about 1.4 to 1.6 IV).

In another embodiment, the polymer formulation comprises 70% by weight triblock poly L-lactide-co-PEG (95/5 to 99/01, or from about 98/2 to 99/01) (2,000 to 100 Mw PEG, or 6,000 to 8000 Mw PEG) with the poly L-lactide-co-TMC (70/30) (1.4 to 1.6 IV). The polymer composition may also comprise a formulation of about 70% by weight diblock poly L-lactide-co-PEG-MME (95/05 to 99/01) (2,000 to 100 Mw PEG-MME, or 6,000 to 8,000 Mw PEG-MME) with poly L-lactide-co-TMC (70/30 w/w) (1.4 to 1.6 IV).

Pharmaceutical compositions may be incorporated with the polymers by for example grafting to the polymer active sites, impregnating or encapsulating within the polymer composition prior to forming the medical device so as to integrate the composition within the walls of the device and/or coating the medical device one formed on the surface of the device, in particular the abluminal surface.

In embodiments disclosed herein, the medical device comprises a stent, which is structurally configured to be deployed into, for example, an artery or a vein, and be able to expand in situ, and conform to the blood vessel lumen the stent may be used to reestablish blood vessel continuity at the site of injury. The stent can be configured to have many different arrangements so that it is crimpable when loading, and expandable and flexible at physiological conditions once deployed. The biodegradable medical device may comprise a base polymer comprising, for example ply L-Lactide or poly D-Lactide, modifying co-polymer(s), such as poly L (or D) lactide-co-Tri-methylene-carbonate or poly L (or D)-lactide-co-e-caprolactone, as described above.

Figure 11A:
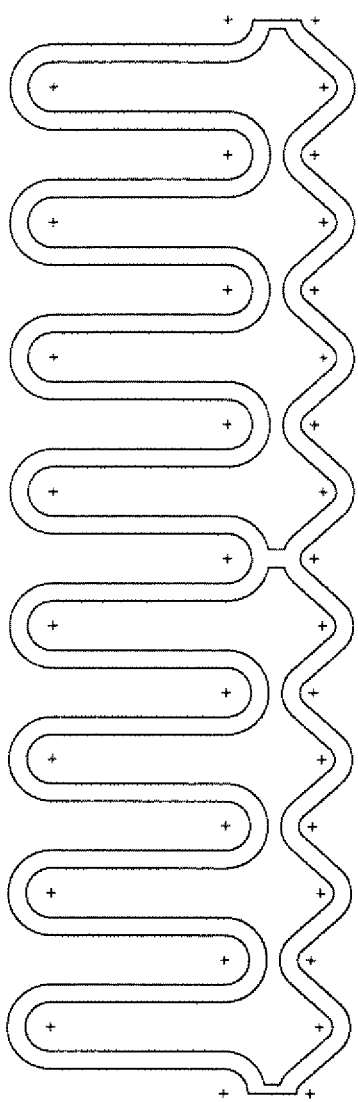
FIG. 11A illustrates a bioabsorbable stent design depicting a folded ring segment and the ring segment in its open configuration.
Figure 11A:
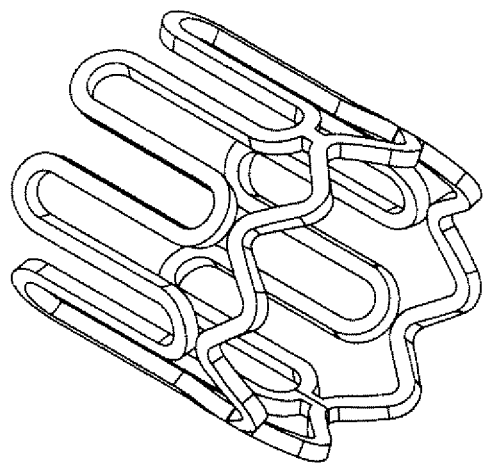
Figure 11B:
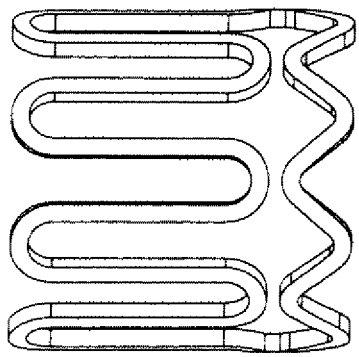
FIG. 11B shows the stent design from an alternate angle.
Figure 11B:
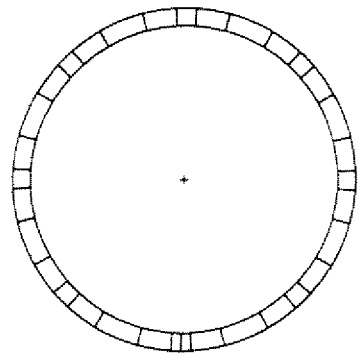
Figure 12A:
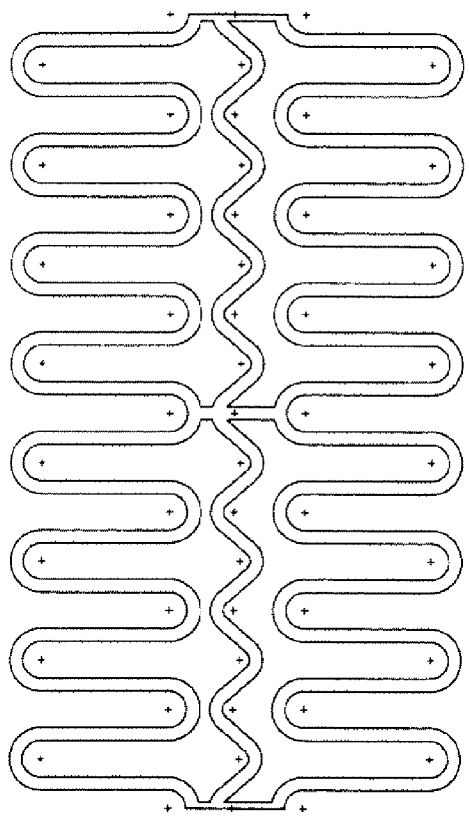
FIG. 12A and FIG. 12B illustrate an alternate bioabsorbable stent design depicting a ring segment in different states.
Figure 12A:
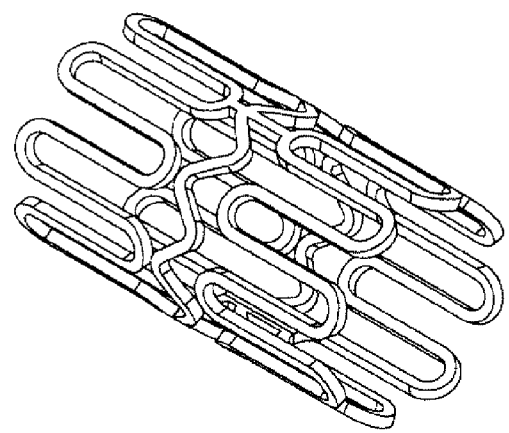
Figure 12B:
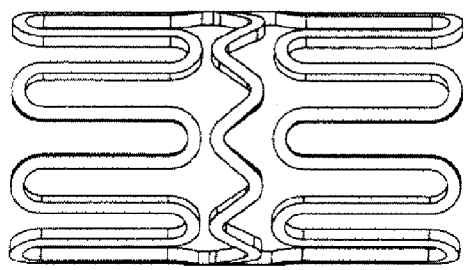
Figure 12B:
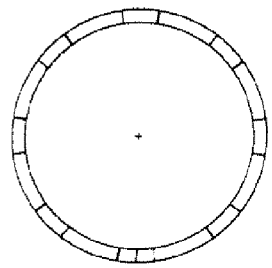
Figure 13:
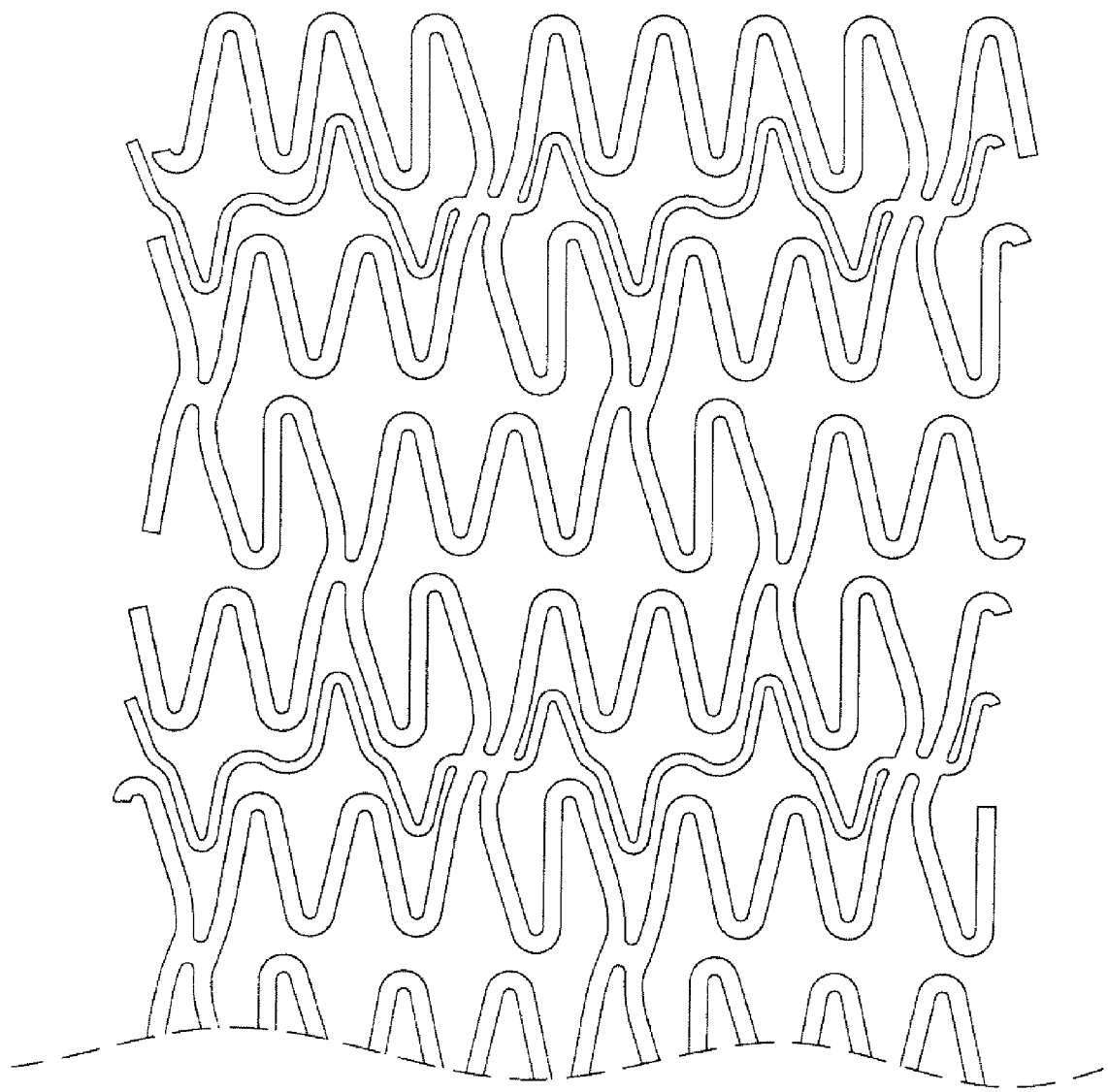
FIG. 13 and FIG. 14 illustrate bioabsorbable stent designs depicting the configuration of the wall of a stent and its segments.
Figure 14:
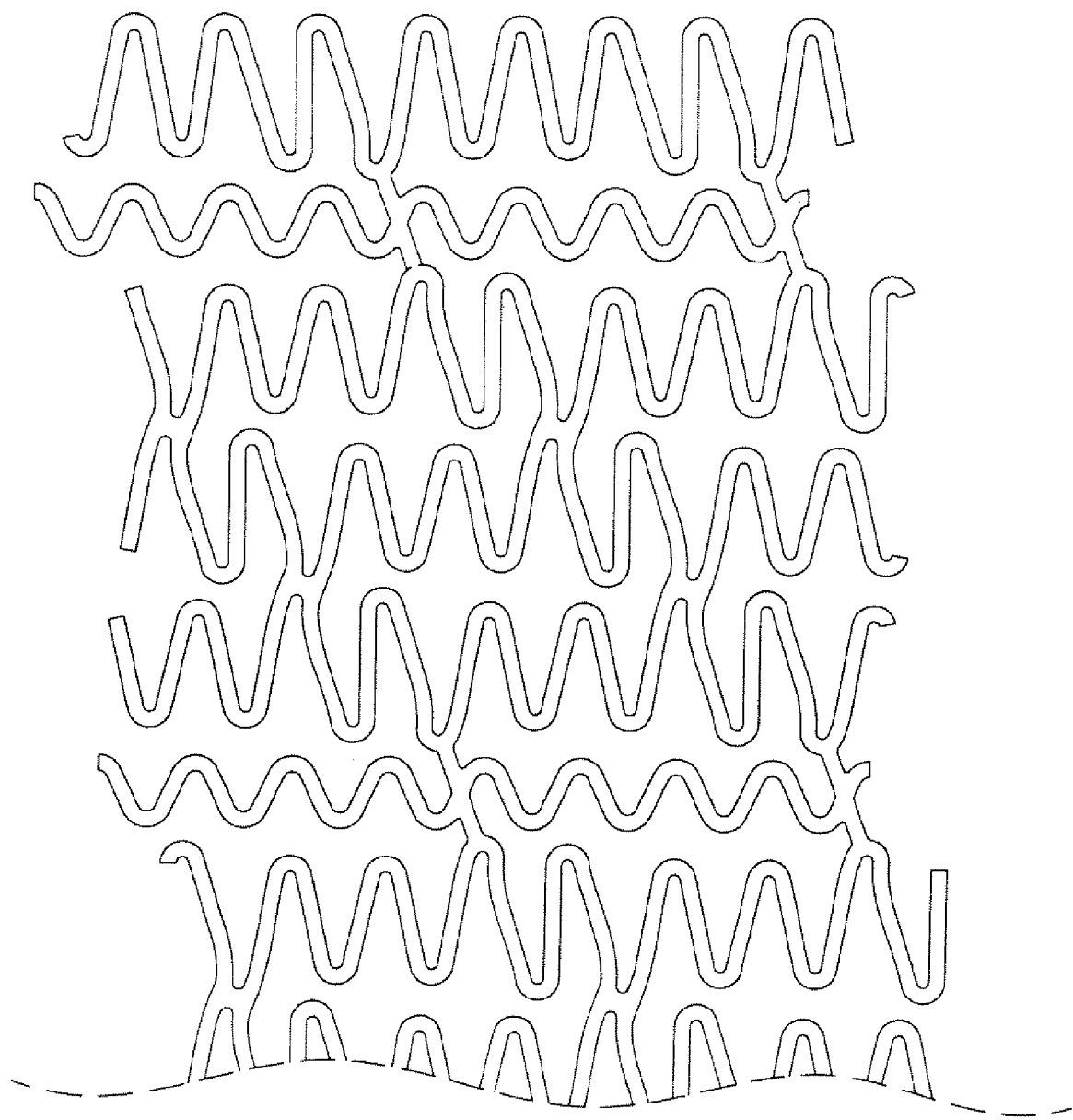
Figure 15:
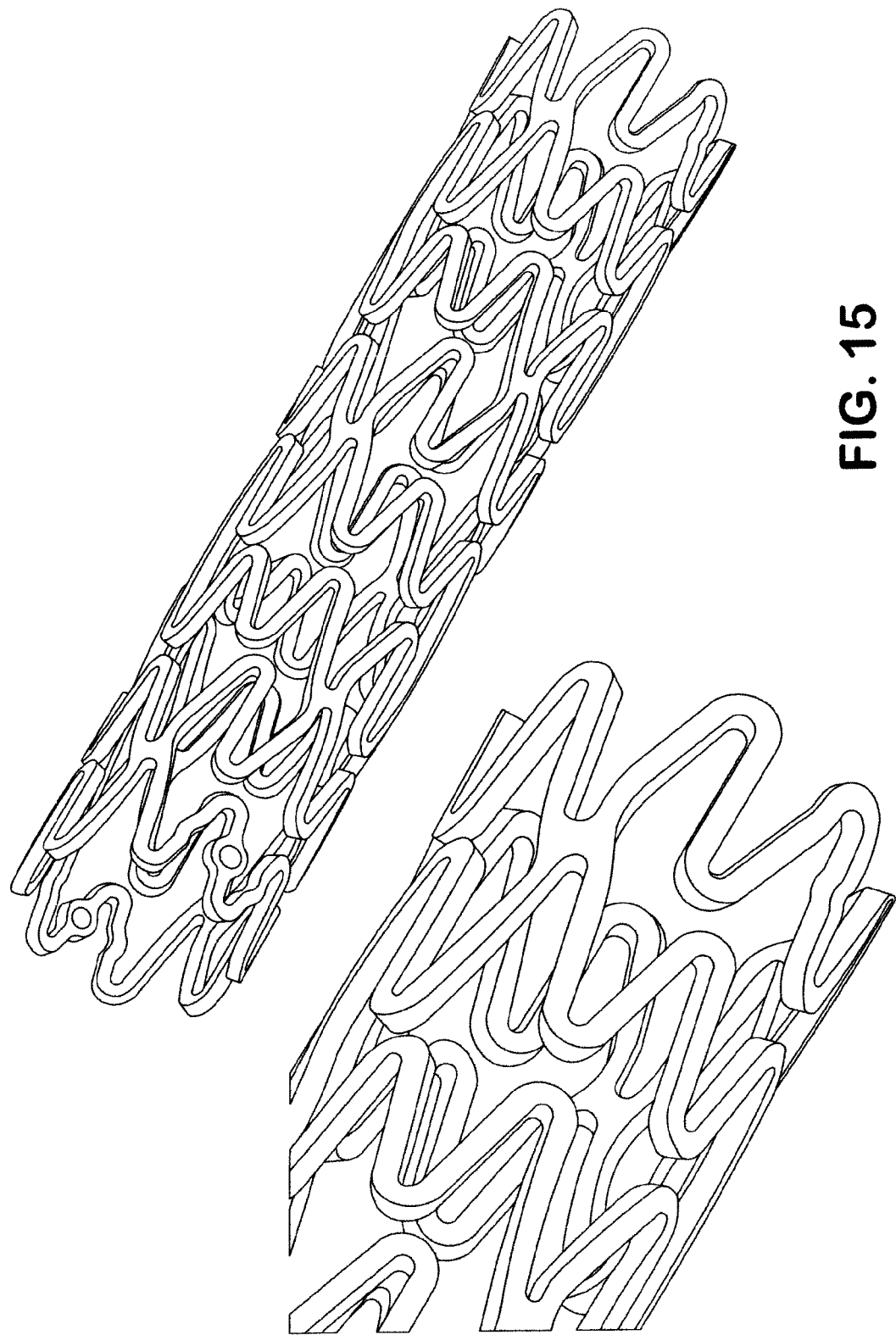
FIG. 15 illustrates a bioabsorbable stent design comprising a radiopaque marker integrated within the stent wall.
Figure 16:
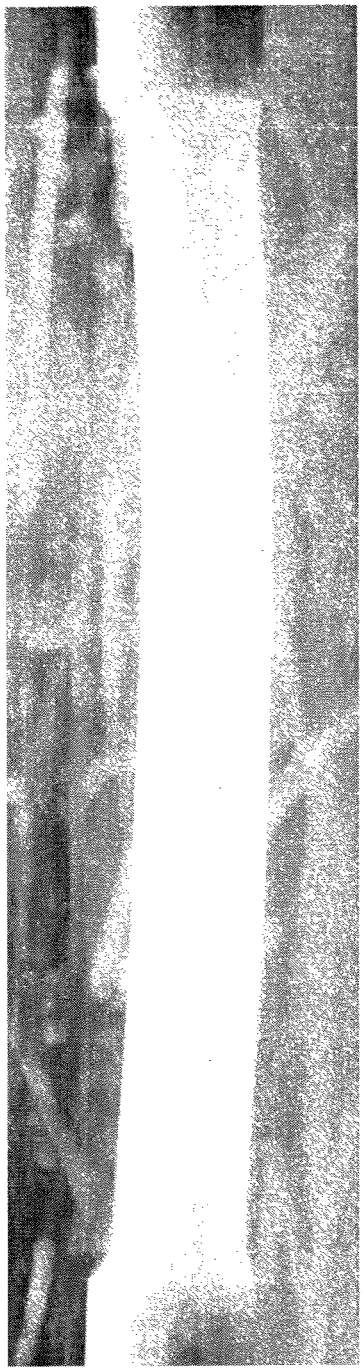
FIG. 16 illustrates a bioabsorbable stent design depicting a the average body collapse pressure.
Figure 17:
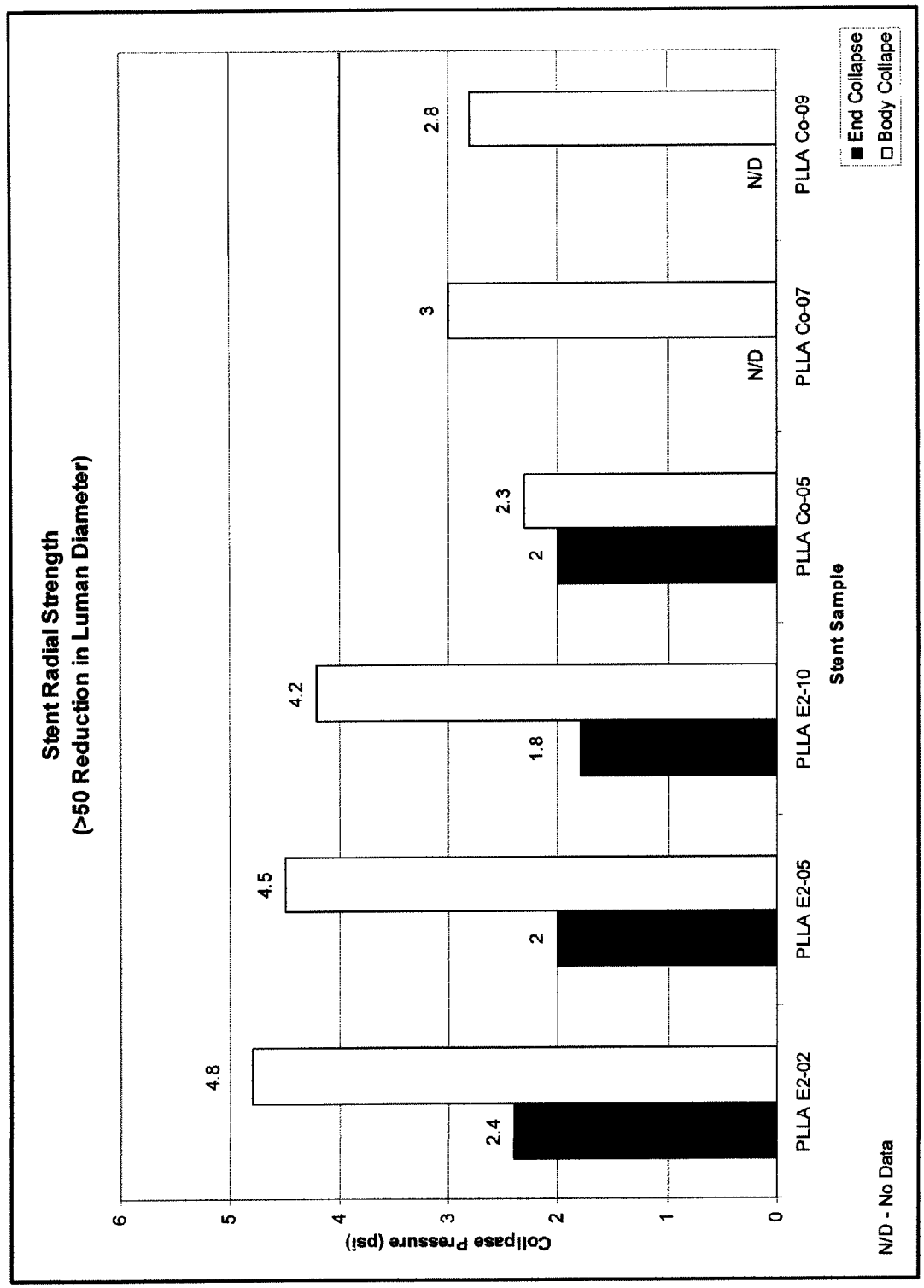
FIG. 17 is a bar graph illustrating data depicting the radial strength of bioabsorbable stents.
Figure 18:
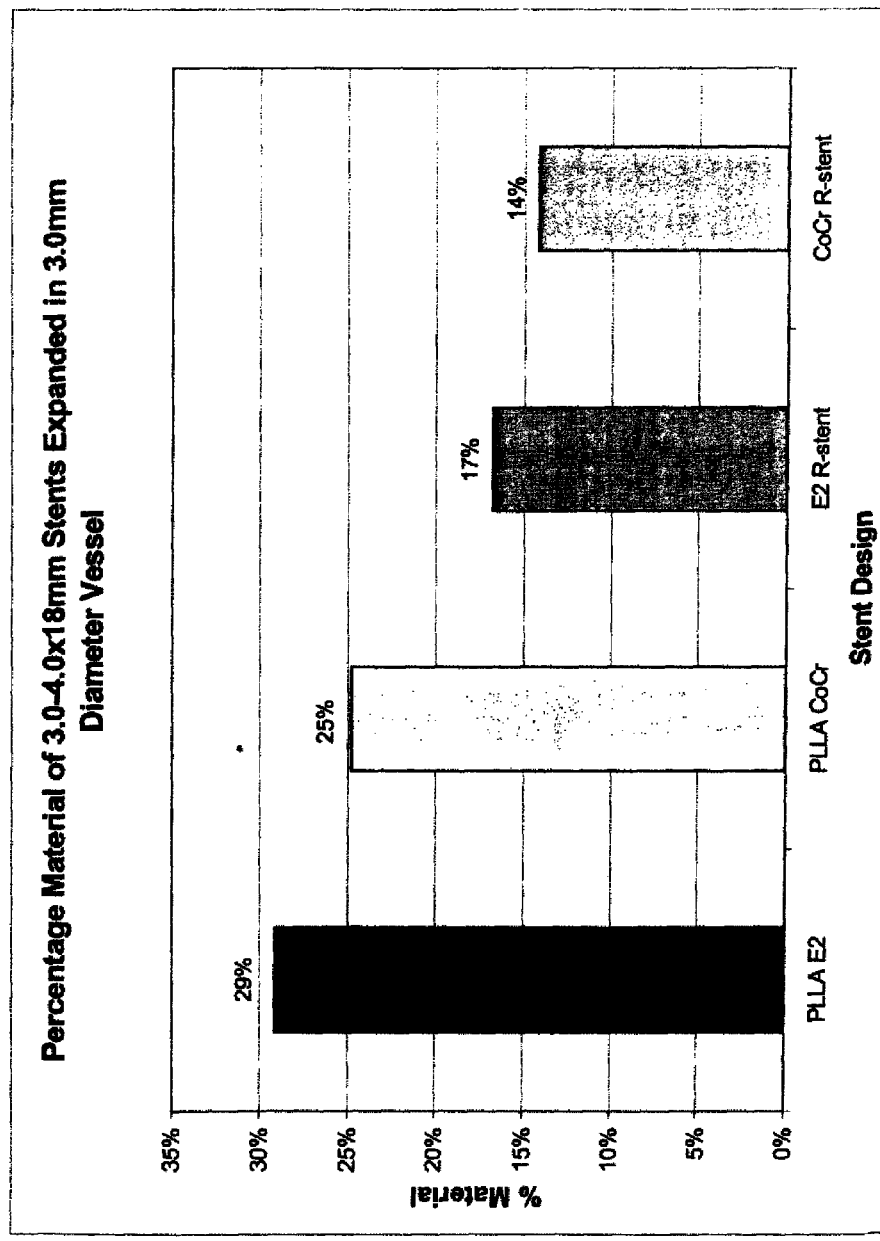
FIG. 18 illustrates is a bar graph illustrating data depicting the percent material of bioabsorbable stents expanded in blood vessels.
Figure 19:
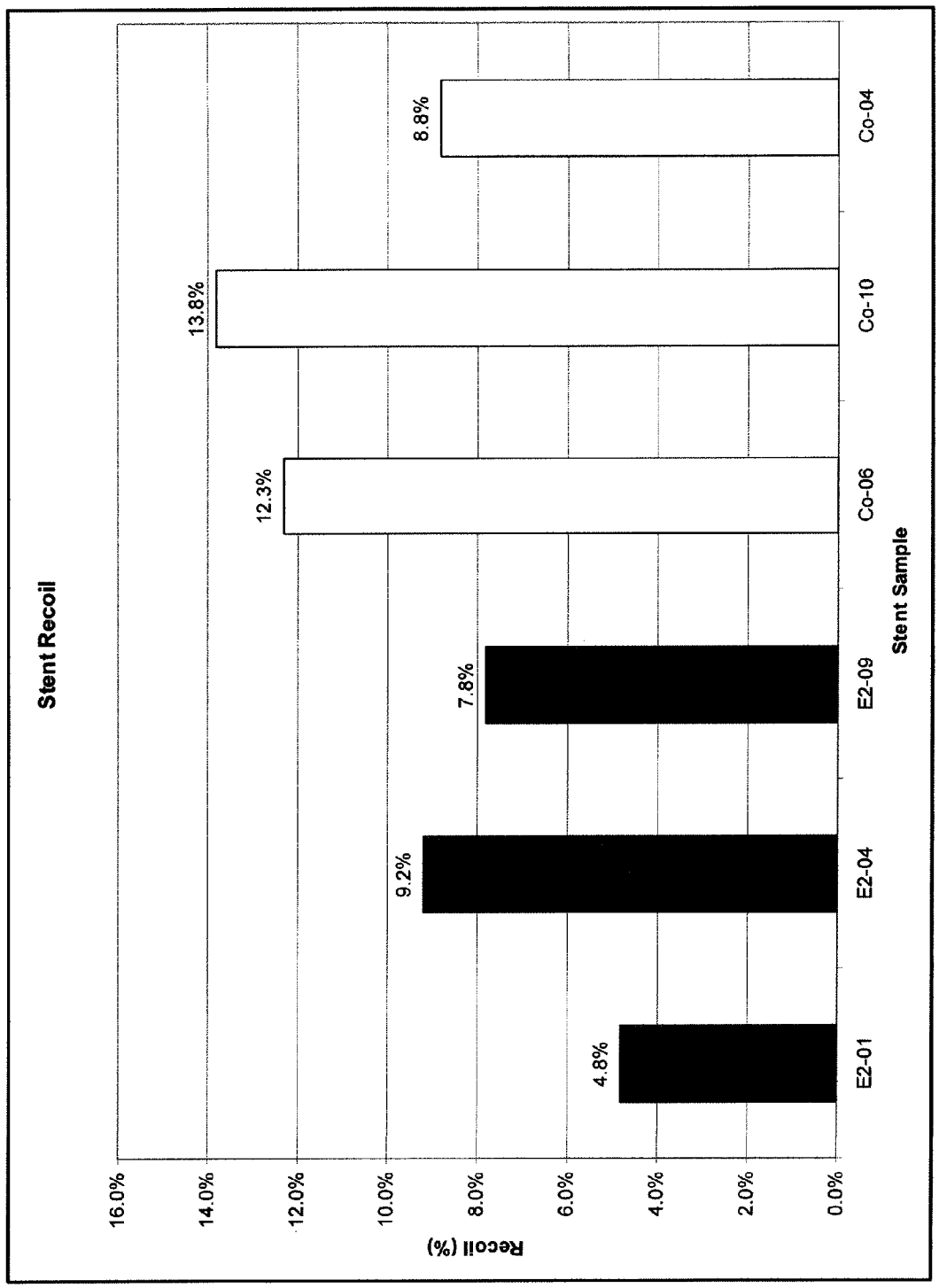
FIG. 19 is a bar graph illustrating data depicting percent stent recoil.
Figure 20:
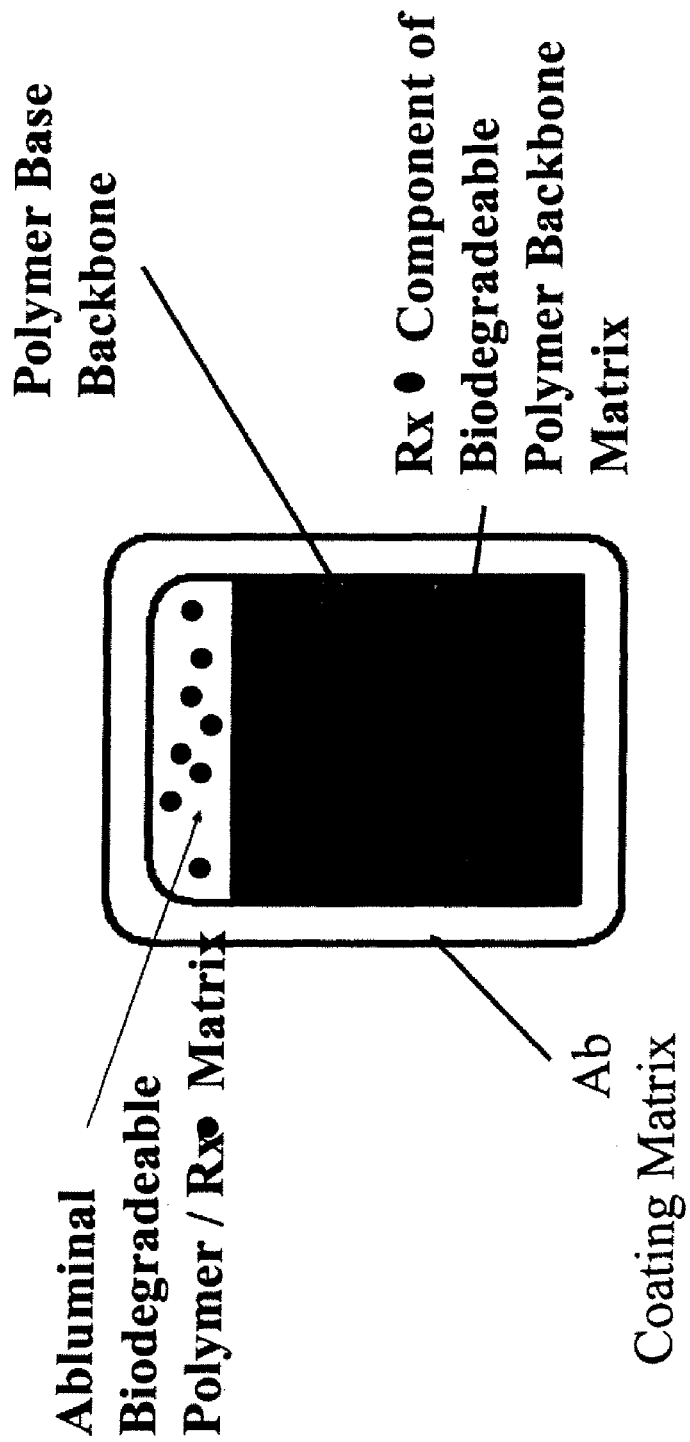
FIG. 20 illustrates a schematic representation of a bioabsorbable stent strut in cross section, which comprises a stent configuration having encapsulated pharmaceutical composition within the struts. In this embodiment, the stent is coated with a matrix comprising an antibody coating and a drug-coated abluminal surface of the device.

Various embodiments of biodegradable polymeric stents, and/or stent walls with different configuration are illustrated in FIGS. 1-15. For example, the stent is a tubular structure comprising struts operably designed to allow blood to traverse its walls so that the adjacent tissues are bathed or come in contact with it as blood flows through the area. The particular stent designs selected may depend on the size of the stent radially and longitudinally. FIG. 11A illustrates a scaffold wherein a number of looped structures are positioned above a collapsable/expandable suspension strut as illustrated in FIG. 11A the looped structures a . . . an expand along an axis and suspension strut b is expanded along the same axis. Suspension strut b may be constructed so as to form a closed loop, such as a circumferential loop as shown at FIGS. 11A and 11B; and FIG. 12A and FIG. 12B. The cross-linking strut of the unrolled scaffold of FIG. 11a may maintain higher loop strength. FIG. 15 shows a tube structure embodiment employing such technology; other shapes such as conical, or bifurcated, are also envisioned.

Scaffolds of the present inventions may find employment in many biological areas including, without limitation, the trachea, bracial, fallopian tube, esophagous, and vasculature. Scaffolds may comprise or may be coated with, any type of drug such as hormones, serp-1, MPA etc.

Scaffold elements may be configured to prematurely deform to their maximum length and/or structure and then plastically elongate to form or create a second structure within which has different mechanical properties when compared to the primary structure of the composite structure. Over stretching of the structure may be advantageous to enable alignment of crystalline structures, thereby increasing structural strength. The secondary structure within the primary structure may allow, for example, a bifurcated shape. The secondary structure would allow changes in structures beyond that allowed by simple plastic deformation.

A method of the invention comprises a method for making a bioabsorbable polymeric implant comprising: (a) blending a polymer composition comprising a crystallizable composition comprising a base polymer of poly L-lactide or poly D-lactide linked with modifying copolymers comprising poly L (or D)-lactide-co-Tri-methylene-carbonate or poly L (or D)-lactide-co-e-caprolactone in the form of block copolymers or as blocky random copolymers wherein the lactide chain length is sufficiently long enough to allow cross-moiety crystallization; (b) molding said polymer composition to structurally configure said implant; and (c) cutting said implant.

In one embodiment, the blended form is molded in the form of a tube defining a lumen therein. The tube may then be cut using laser, air knife, or mechanical means, or the like, to form the desired design, such as a stent scaffold. In another embodiment, the blended form is molded into sheets. The sheets are then cut using a laser, air knife, or mechanical means, or the like, to the desired design. If desired, the designed cut sheet may then be welded, annealed, engaged, etc. with another portion of the sheet to form the overall structure desired. For example, the designed, cut, sheet may be rolled into a tubular form and welded along a seam, forming a tube that may later be cut into stents, etc. The sheet itself may be coated on one or both sides with a material, in particular a composition comprising a biological or pharmacological agent. One side may have a coating formed of a different matrix and/or different biological or pharmacological agent or agents.

A method for fabricating the medical device may comprise: (a) preparing a biodegradable polymeric structure; (b) designing said polymeric structure to be configured to allow for implantation into a patient; (c) cutting said structure into patterns configured to permit traversing of the device through openings and to allow for crimping of the device.

The medical device of the invention can be any device used for implanting into an organ or body part comprising a lumen, and can be, but is not limited to, a stent, a stent graft, a synthetic vascular graft, a heart valve, a catheter, a vascular prosthetic filter, a pacemaker, a pacemaker lead, a defibrillator, a patent foramen ovale (PFO) septal closure device, a vascular clip, a vascular aneurysm occluder, a hemodialysis graft, a hemodialysis catheter, an atrioventricular shunt, an aortic aneurysm graft device or components, a venous valve, a sensor, a suture, a vascular anastomosis clip, an indwelling venous or arterial catheter, a vascular sheath and a drug delivery port. The medical device can be made of numerous bioabsorbable materials depending on the device, biodegradable materials such as polylactide polymers and polyglycolide polymers or copolymers thereof are the most suitable.

In one embodiment, the medical device comprises a coating comprising a matrix which comprises a nontoxic, biocompatible, bioerodible and biodegradable synthetic material. The coating may further comprise one or more pharmaceutical substances or drug compositions for delivering to the tissues adjacent to the site of implantation, and one or more ligands, such as a peptide, small and/or large molecules, and/or antibodies or combinations thereof for capturing and immobilizing progenitor endothelial cells on the blood contacting surface of the medical device.

In one embodiment, the implantable medical device comprises a stent with a coating. In accordance with one embodiment, the stent is an expandable intraluminal endoprosthesis designed and configured to have a surface for attaching a coating for controlled or slow release of a therapeutic substance to adjacent tissues.

In one embodiment, the controlled-release matrix can comprise one or more polymers and/or oligomers from various types and sources, including, natural or synthetic polymers, which are biocompatible, biodegradable, bioabsorbable and useful for controlled-released of the medicament. For example, in one embodiment, the naturally occurring polymeric materials can include proteins such as collagen, fibrin, tropoelastin, elastin, cross-linked tropoelastin and extracellular matrix component, or other biologic agents or mixtures thereof. In this embodiment of the invention, the naturally-occurring material can be made by genetic engineering techniques from exogenous genes carried by vectors, such as a plasmid vector and engineered into a host, such as a bacterium. In this embodiment, desired polymer proteins such as tropoelastin and elastin can be produced and isolated for use in the matrix. In alternate embodiments, the naturally occurring polymeric matrices can be purified from natural sources by known methods or they can be obtained by chemical synthesis of the protein polymer. In certain embodiments, the naturally occurring material can be chemically modified or synthesized, for example, by cross-linking the material such as proteins, or by methylation, phosphorylation and the like. In another embodiment, the matrix can comprise a denuded blood vessel or blood vessel scaffolds and/or components thereof.

In one embodiment, the matrix may comprise a synthetic material which can include polyesters such as polylactic acid, polyglycolic acid or copolymers and or combinations thereof, a polyanhydride, polycaprolactone, polyhydroxybutyrate valerate, polydixanone, and other biodegradable polymer, or mixtures or copolymers thereof. In this embodiment, the matrix comprises poly(lactide-coglycolide) as the matrix polymer for coating the medical device. In this embodiment, the poly(lactide-co-glycolide) composition comprises at least one polymer of poly-DL-co-glycolide or copolymer or mixtures thereof, and it is mixed together with the pharmaceutical substances to be delivered to the tissues. The coating composition is then applied to the surface of the device using standard techniques such as spraying, dipping, and/or chemical vaporization. Alternatively, the poly(lactide-co-glycolide) (PGLA) solution can be applied as a single layer separating a layer or layers of the pharmaceutical substance(s).

In another embodiment, the coating composition further comprises pharmaceutically acceptable polymers and/or pharmaceutically acceptable carriers, for example, nonabsorbable polymers, such as ethylene vinyl acetate (EVAC) and methylmethacrylate (MMA). The nonabsorbable polymer, for example, can aid in further controlling release of the substance by increasing the molecular weight of the composition thereby delaying or slowing the rate of release of the pharmaceutical substance.

In certain embodiments, the polymer material or mixture of various polymers can be applied together as a composition with the pharmaceutical substance on the surface of the medical device and can comprise a single layer. Multiple layers of composition can be applied to form the coating. In another embodiment, multiple layers of polymer material or mixtures thereof can be applied between layers of the pharmaceutical substance. For example, the layers may be applied sequentially, with the first layer directly in contact with the uncoated surface of the device and a second layer comprising the pharmaceutical substance and having one surface in contact with the first layer and the opposite surface in contact with a third layer of polymer which is in contact with the surrounding tissue. Additional layers of the polymer material and drug composition can be added as required, alternating each component or mixtures of components thereof.

In another embodiment, the matrix may comprise non-polymeric materials such as nanoparticles formed of, for example, metallic alloys or other materials. In this embodiment, the coating on the medical device can be porous and the pharmaceutical substances can be trapped within and between the particles. In this embodiment, the size of the particles can be varied to control the rate of release of the pharmaceutical substance trapped in the particles depending on the need of the patient. In one embodiment, the pharmaceutical composition can be a slow/controlled-release pharmaceutical composition.

Alternatively, the pharmaceutical substance of the coating can be applied as multiple layers of a composition and each layer can comprise one or more drugs surrounded by polymer material. In this embodiment, the multiple layers of pharmaceutical substance can comprise a pharmaceutical composition comprising multiple layers of a single drug; one or more drugs in each layer, and/or differing drug compositions in alternating layers applied. In one embodiment, the layers comprising pharmaceutical substance can be separated from one another by a layer of polymer material. In another embodiment, a layer of pharmaceutical composition may be provided to the device for immediate release of the pharmaceutical substance after implantation.

In one embodiment, the pharmaceutical substance or composition may comprise one or more drugs or substances which can inhibit smooth muscle cell migration and proliferation at the site of implantation, can inhibit thrombus formation, can promote endothelial cell growth and differentiation, and/or can inhibit restenosis after implantation of the medical device. Additionally, the capturing of the progenitor endothelial cells on the luminal surface of the medical device accelerates the formation of a functional endothelium at the site of injury.

Examples of compounds or pharmaceutical compositions which can be incorporated in the matrix, and/or impregnated into the medical device include, but are not limited to prostacyclin, prostacyclin analogs, $\alpha$-CGRP, $\alpha$-CGRP analogs or $\alpha$-CGRP receptor agonists; prazosin; monocyte chemoattactant protein-1 (MCP-1); immunosuppressant drugs such as rapamycin, drugs which inhibit smooth muscle cell migration and/or proliferation, antithrombotic drugs such as thrombin inhibitors, immunomodulators such as platelet factor 4 and CXC-chemokine; inhibitors of the CX3CR1 receptor family; antiinflammatory drugs, steroids such as dihydroepiandrosterone (DHEA), testosterone, estrogens such as 17$\beta$-estradiol; statins such as simvastatin and fluvastatin; PPAR-alpha ligands such as fenofibrate and other lipid-lowering drugs, PPAR-delta and PPAR-gamma agonists such as rosiglitazone; PPAR-dual-$\alpha\gamma$ agonists, LBM-642, nuclear factors such as NF-$\kappa\beta$, collagen synthesis inhibitors, vasodilators such as acetylcholine, adenosine, 5-hydroxytryptamine or serotonin, substance P, adrenomedulin, growth factors which induce endothelial cell growth and differentiation such as basic fibroblast growth factor (bFGF), platelet-derived growth factor (PDGF), endothelial cell growth factor (EGF), vascular endothelial cell growth factor (VEGF); protein tyrosine kinase inhibitors such as Midostaurin and imatinib or any anti-angiogenesis inhibitor compound; peptides or antibodies which inhibit mature leukocyte adhesion, antibiotics/antimicrobials, and other substances such as tachykinins, neurokinins or sialokinins, tachykinin NK receptor agonists; PDGF receptor inhibitors such as MLN-518 and derivatives thereof, butyric acid and butyric acid derivatives puerarin, fibronectin, erythropoietin, darbepotin, serine proteinase-1 (SERP-1) and the like. The aforementioned compounds and pharmaceutical substances can be applied to the coating on the device alone or in combinations and/or mixtures thereof.

In one embodiment, the implantable medical device can comprise a coating comprising one or more barrier layers in between said one or more layers of matrix comprising said pharmaceutical substances. In this embodiment, the barrier layer may comprise a suitable biodegradable material, including but not limited to suitable biodegradable polymers including: polyesters such as PLA, PGA, PLGA, PPF, PCL, PCC, TMC and any copolymer of these; polycarboxylic acid, polyanhydrides including maleic anhydride polymers; polyorthoesters; poly-amino acids; polyethylene oxide; polyphosphazenes; polylactic acid, polyglycolic acid and copolymers and mixtures thereof such as poly(L-lactic acid) (PLLA), poly(D,L-lactide), poly(lactic acid-co-glycolic acid), 50/50 (DL-lactide-co-glycolide); polydixanone; polypropylene fumarate; polydepsipeptides; polycaprolactone and co-polymers and mixtures thereof such as poly(D, L-lactide-co-caprolactone) and polycaprolactone co-butylacrylate; polyhydroxybutyrate valerate and blends; polycarbonates such as tyrosine-derived polycarbonates and arylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate. The number of barrier layers that the coating on a device may have depends on the amount of therapeutic needed as dictated by the therapy required by the patient. For example, the longer the treatment, the more therapeutic substance required over a period of time, the more barrier layers to provide the pharmaceutical substance in a timely manner.

In one embodiment, the coating comprises a ligand which is applied to the blood contacting surface of the medical device and the ligand specifically recognizes and binds a desired component or epitope on the surface of target cells in the circulating blood. In one embodiment, the ligand is specifically designed to recognize and bind only the genetically-altered mammalian cell by recognizing only the genetically-engineered marker molecule on the cell membrane of the genetically-altered cells. The binding of the target cells immobilizes the cells on the surface of the device.

In alternate embodiment, the ligand on the surface of the medical device for binding the genetically-altered cell is selected depending on the genetically engineered cell membrane marker molecule. That is, the ligand binds only to the cell membrane marker molecule or antigen which is expressed by the cell from extrachromosomal genetic material provided to the cell so that only the genetically-modified cells can be recognized by the ligand on the surface of the medical device. In this manner, only the genetically-modified cells can bind to the surface of the medical device. For example, if the mammalian cell is an endothelial cell, the ligand can be at least one type of antibody, antibody fragments or combinations thereof, the antibody is specifically raised against a specific target epitope or marker molecule on the surface of the target cell. In this aspect of the invention, the antibody can be a monoclonal antibody, a polyclonal antibody, a chimeric antibody, or a humanized antibody which recognizes and binds only to the genetically-altered endothelial cell by interacting with the surface marker molecule and, thereby modulating the adherence of the cells onto the surface of the medical device. The antibody or antibody fragment of the invention can be covalently or noncovalently attached to the surface of the matrix, or tethered covalently by a linker molecule to the outermost layer of the matrix coating the medical device. In this embodiment, for example, the monoclonal antibodies can further comprises Fab or F(ab')2 fragments. The antibody fragment of the invention comprises any fragment size, such as large and small molecules which retain the characteristic to recognize and bind the target antigen as the antibody.

In another embodiment, the antibody or antibody fragment of the invention recognize and bind antigens with specificity for the mammal being treated and their specificity is not dependent on cell lineage. In one embodiment, for example, in treating restenosis wherein the cells may not be genetically modified to contain specific cell membrane marker molecules, the antibody or fragment is specific for selecting and binding circulating progenitor endothelial cell surface antigen such as CD133, CD34, CD14, CDw90, CD117, HLA-DR, VEGFR-1, VEGFR-2, Muc-18 (CD146), CD130, stem cell antigen (Sca-1), stem cell factor 1 (SCF/c-Kit ligand), Tie-2, MHC such as H-2Kk and HLA-DR antigen.

In another embodiment, the coating of the medical device comprises at least one layer of a biocompatible matrix as described above, the matrix comprises an outer surface for attaching a therapeutically effective amount of at least one type of small molecule of natural or synthetic origin. The small molecule recognizes and interacts with, for example, progenitor endothelial cells in the treatment of restenosis, to immobilize the cells on the surface of the device to form an endothelial layer. The small molecules can be used in conjunction with the medical device for the treatment of various diseases, and can be derived from a variety of sources such as cellular components such as fatty acids, proteins, nucleic acids, saccharides and the like and can interact with an antigen on the surface of a progenitor endothelial cell with the same results or effects as an antibody. In this aspect of the invention, the coating on the medical device can further comprise a compound such as a growth factor as described herewith in conjunction with the coating comprising an antibody or antibody fragment.

In another embodiment, the coating of the medical device comprises at least one layer of a biocompatible matrix as described above, the matrix comprising a luminal surface for attaching a therapeutically effective amount of at least one type of small molecule of natural or synthetic origin. The small molecule recognizes and interacts with an antigen on the target cell such as a progenitor endothelial cell surface to immobilize the progenitor endothelial cell on the surface of the device to form endothelium. The small molecules can be derived from a variety of sources such as cellular components including, fatty acids, peptides, proteins, nucleic acids, saccharides and the like and can interact, for example, with a structure such as an antigen on the surface of a progenitor endothelial cell with the same results or effects as an antibody.

In another embodiment, there is provided a method for treating vascular disease such as restenosis and artherosclerosis, comprising administering a pharmaceutical substance locally to a patient in need of such substance. The method comprises implanting into a vessel or hollowed organ of a patient a medical device with a coating, which coating comprises a pharmaceutical composition comprising a drug or substance for inhibiting smooth muscle cell migration and thereby restenosis, and a biocompatible, biodegradable, bioerodible, nontoxic polymer or non-polymer matrix, wherein the pharmaceutical composition comprises a slow or controlled-release formulation for the delayed release of the drug. The coating on the medical device can also comprise a ligand such as an antibody for capturing cells such as endothelial cells and or progenitor cells on the luminal surface of the device so that a functional endothelium is formed.

In another embodiment, there is provided a method of making a coated medical device or a medical device with a coating, which comprises applying to a surface of a medical device a polymer or non-polymer matrix and a pharmaceutical composition comprising one or more drugs, and applying a ligand to the medical device so that the ligand attaches to a surface of the device and is designed to bind molecules on the cell membrane of circulating native or genetically engineered cells. In this embodiment, the polymer matrix comprises a biocompatible, biodegradable, nontoxic polymer matrix such as collagen, tropocollagen, elastin, tropoelastin, cross-linked tropoelastin, poly(lactide-co-glycolide) copolymer, polysaccharides and one or more pharmaceutical substances, wherein the matrix and the substance(s) can be mixed prior to applying to the medical device. In this embodiment, at least one type of ligand is applied to the surface of the device and can be added on top or on the outer surface of the device with the drug/matrix composition in contact with the device surface. The method may alternatively comprise the step of applying at least one layer of a pharmaceutical composition comprising one or more drugs and pharmaceutically acceptable carriers, and applying at least one layer of a polymer matrix to the medical device.

In one embodiment, the matrix can be applied as one or more layers and with or without the pharmaceutical substance, and the ligand can be applied independently to the medical device by several methods using standard techniques, such as dipping, spraying or vapor deposition. In an alternate embodiment, the polymer matrix can be applied to the device with or without the pharmaceutical substance. In this aspect of the invention wherein a polymer matrix is applied without the drug, the drug can be applied as a layer between layers of matrices. In other embodiments, a barrier layer is applied between the layers comprising the pharmaceutical substances.

In one embodiment, the method comprises applying the pharmaceutical composition as multiple layers with the ligand applied on the outermost surface of the medical device so that the ligand such as antibodies can be attached in the luminal surface of the device. In one embodiment, the method for coating the medical device comprises: applying to a surface of said medical device at least one or more layers of a matrix, one or more pharmaceutical substance(s), and a basement membrane component; applying to said at least one layer of said composition on said medical device a solution comprising at least one type of ligand for binding and immobilizing genetically-modified target cells; and drying said coating on the stent under vacuum at low temperatures.

In another embodiment, the coating is comprised of a multiple component pharmaceutical composition within the matrix such as containing a fast release pharmaceutical agent to retard early neointimal hyperplasia/smooth muscle cell migration and proliferation, and a secondary biostable matrix that releases a long acting agent for maintaining vessel patency or a positive blood vessel remodeling agent, such as endothelial nitric oxide synthase (eNOS), nitric oxide donors and derivatives such as aspirin or derivatives thereof, nitric oxide producing hydrogels, PPAR agonist such as PPAR-α ligands, tissue plasminogen activator, statins such as atorvastatin, erythropoietin, darbepotin, serine proteinase-1 (SERP-1) and pravastatin, steroids, and/or antibiotics.

The figures provided herewith depict embodiments that are described as illustrative examples that are not deemed in any way as limiting the present invention.

While the invention has been particularly shown and described with reference to particular embodiments, it will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

I claim:

1. A method for fabricating a cardiovascular expandable scaffold comprising:
    blending a polymer composition comprising a crystallizable composition comprising a base polymer of poly L-lactide, and/or poly D-lactide, and/or poly L-lactide-co-PEG, and/or poly D-lactide-co-PEG, linked with modifying copolymers comprising poly L (or D)-lactide-co-Tri-methylene-carbonate or poly L (or D)-lactide-co-ε-caprolactone in the form of block copolymers or as blocky random copolymers;
    molding said polymer composition to structurally configure said scaffold;
    coating said polymer scaffold with a pharmaceutical composition comprising a ligand; and
    cutting said scaffold to form desired patterns;
    wherein the polymer scaffold is configured in the form of a continuously interconnected scaffold of struts which is crystallizable when stretched by expansion and wherein the polymer of poly L-lactide and poly D-lactide form a racemate-type cross-moiety crystallization.

2. The method of claim 1, wherein the blending further comprises blending a pharmacological and/or biological agent and/or radioopaque or radio-detectable material into the polymer composition.

3. The method of claim 2, wherein the pharmacological agent is selected from the group consisting of: cyclosporin A, mycophenolic acid, mycophenolate mofetil acid, rapamycin, rapamycin derivatives, biolimus A9, CCI-779, RAD 001, AP23573, azathioprene, tacrolimus (FK506), tranilast, dexamethasone, corticosteroid, everolimus, pimecrolimus, retinoic acid, vitamin E, rosglitazone, simvastatins, fluvastatin, estrogen, 17β-estradiol, hydrocortisone, acetaminophen, ibuprofen, naproxen, fluticasone, clobetasol, adalimumab, sulindac, dihydroepiandrosterone, testosterone, puerarin, platelet factor 4, basic fibroblast growth factor, fibronectin, butyric acid, butyric acid derivatives, paclitaxel, paclitaxel derivatives, LBM-642, deforolimus, and probucol.

4. The method of claim 2, wherein the biological agent is selected from the group consisting of: antibiotics/antimicrobials, antiproliferative agents, antineoplastic agents, antioxidants, endothelial cell growth factors, smooth muscle cell growth and/or migration inhibitors, thrombin inhibitors, immunosuppressive agents, anti-platelet aggregation agents, collagen synthesis inhibitors, therapeutic antibodies, nitric oxide donors, antisense oligonucleotides, wound healing agents, therapeutic gene transfer constructs, peptides, proteins, extracellular matrix components, vasodialators, thrombolytics, anti-metabolites, growth factor agonists, antimitotics, steroids, steroidal antiinflammatory agents, chemokines, proliferator-activated receptor-gamma agonists, proliferator-activated receptor-alpha agonists proliferator-activated receptor-beta agonists, proliferator-activated receptor-alpha/beta agonists, proliferator-activated receptor-delta agonists, NFκβ, proliferator-activated receptor-alpha-gamma agonists, nonsteroidal antiinflammatory agents, angiotensin converting enzyme (ACE) inhibitors, free radical scavengers, inhibitors of the CX3CR1 receptor and anti-cancer chemotherapeutic agents.

5. The method of claim 1, wherein the ligand comprises a small molecule, a peptide, an antibody, an antibody fragment, or combinations thereof.

6. The method of claim 5, wherein the antibody or antibody fragment is specific for a progenitor endothelial cell surface antigen.

7. The method of claim 6, wherein the progenitor endothelial cell surface antigen is selected from the group consisting of CD34, CD45, CD133, CD14, CDw90, CD117, HLA-DR, VEGFR-1, VEGFR-2, CD146, CD130, CD131, stem cell antigen, stem cell factor 1, Tie-2, MCH-H-2Kk and MCH-HLA-DR.

* * * * *